United States Patent
Nakamura et al.

(10) Patent No.: US 10,488,208 B2
(45) Date of Patent: Nov. 26, 2019

(54) COMMUNICATION SYSTEM, CONTROL METHOD, AND STORAGE MEDIUM

(71) Applicant: SONY CORPORATION, Tokyo (JP)

(72) Inventors: Takatoshi Nakamura, Tokyo (JP); Akira Tange, Tokyo (JP); Masakazu Yajima, Chiba (JP); Mitsuru Takehara, Tokyo (JP); Yasunori Kamada, Kanagawa (JP); Katsuhisa Aratani, Kanagawa (JP); Kazunori Hayashi, Tokyo (JP); Takayasu Kon, Tokyo (JP); Kohei Asada, Kanagawa (JP); Kazuhiro Watanabe, Tokyo (JP); Tsuyoshi Abiko, Saitama (JP); Yuki Koga, Tokyo (JP); Tomoya Onuma, Shizuoka (JP)

(73) Assignee: SONY CORPORATION, Tokyo (JP)

( * ) Notice: Subject to any disclaimer, the term of this patent is extended or adjusted under 35 U.S.C. 154(b) by 340 days.

(21) Appl. No.: 15/302,093

(22) PCT Filed: Jan. 20, 2015

(86) PCT No.: PCT/JP2015/051411
§ 371 (c)(1),
(2) Date: Oct. 5, 2016

(87) PCT Pub. No.: WO2015/162949
PCT Pub. Date: Oct. 29, 2015

(65) Prior Publication Data
US 2017/0205240 A1 Jul. 20, 2017

(30) Foreign Application Priority Data
Apr. 21, 2014 (JP) ................................. 2014-087608

(51) Int. Cl.
*G01C 21/34* (2006.01)
*G01C 21/26* (2006.01)
(Continued)

(52) U.S. Cl.
CPC .......... *G01C 21/3407* (2013.01); *A61B 5/165* (2013.01); *G01C 21/265* (2013.01);
(Continued)

(58) Field of Classification Search
CPC ............ G01C 21/3407; G01C 21/3484; G01C 21/3641; G01C 21/3617; G01C 21/3682;
(Continued)

(56) References Cited

U.S. PATENT DOCUMENTS

| 2009/0115617 | A1 | 5/2009 | Sano et al. | |
| 2012/0150430 | A1* | 6/2012 | French | G01C 21/3415 701/425 |

(Continued)

FOREIGN PATENT DOCUMENTS

| JP | 2007-34664 A | 2/2007 |
| JP | 2009-98446 A | 5/2009 |

(Continued)

OTHER PUBLICATIONS

International Search Report dated Apr. 21, 2015 in PCT/JP15/051411 Filed Jan. 20, 2015.

*Primary Examiner* — Anne M Antonucci
(74) *Attorney, Agent, or Firm* — Xsensus LLP

(57) ABSTRACT

A communication system, a control method, and a storage medium, which can guide a user to an action for having the predetermined feeling in accordance with a feeling map. A communication system including: an acquisition unit configured to acquire present position information of a user; a guiding information generation unit configured to generate guiding information in accordance with the present position (Continued)

information and map information in which feeling data is mapped; and a supply unit configured to supply the guiding information to the user.

12 Claims, 14 Drawing Sheets

(51) Int. Cl.
    *G01C 21/36*     (2006.01)
    *G06K 9/00*     (2006.01)
    *G06F 17/30*     (2006.01)
    *A61B 5/16*     (2006.01)
    *G06F 16/84*     (2019.01)
    *G06F 16/00*     (2019.01)

(52) U.S. Cl.
    CPC ..... *G01C 21/3484* (2013.01); *G01C 21/3617* (2013.01); *G01C 21/3641* (2013.01); *G01C 21/3682* (2013.01); *G06F 16/00* (2019.01); *G06F 16/86* (2019.01); *G06K 9/00892* (2013.01)

(58) Field of Classification Search
    CPC . G01C 21/265; G06F 17/30917; G06F 17/30; A61B 5/165; G06K 9/00892
    See application file for complete search history.

(56) References Cited

U.S. PATENT DOCUMENTS

2014/0250200 A1*   9/2014   Geurts .................. G06Q 50/01
                                                 709/206
2014/0365552 A1   12/2014   Sano et al.
2015/0112581 A1*   4/2015   Hakim ............... G01C 21/3461
                                                 701/400

FOREIGN PATENT DOCUMENTS

JP       2009-188899 A     8/2009
WO     2013/190689 A1    12/2013

* cited by examiner

EXEMPLARY DISPLAY 2

EXEMPLARY DISPLAY 1

EXEMPLARY DISPLAY 4

EXEMPLARY DISPLAY 3

COMMUNICATION SYSTEM, CONTROL METHOD, AND STORAGE MEDIUM

TECHNICAL FIELD

The present disclosure relates to a communication system, a control method, and a storage medium.

BACKGROUND

In recent years, a smartphone, a mobile phone terminal, a tablet terminal, a digital camera, or the like which has a camera function becomes widespread, and photographs captured by these are uploaded to servers in large amounts. Also, metadata that includes position information (image capturing site information) is generally attached to the uploaded photograph data. Also, a wearable device, such as a watch terminal, a list band terminal, and an eyeglass HMD, is also start becoming widespread, and it becomes easy to acquire action logs (also referred to as life logs) on a day-to-day basis, and a large amount of acquired action logs are utilized variously.

Also, in recent years, a situation in which feeling data (information of a psychological state) can be sensed by a device that directly contacts a body is getting prepared. Specifically, feeling (a psychological state such as discomfort, tension, delight, and excitation) is roughly estimated from biometric information such as a perspiration amount and a heart rate.

For example, below Patent Literature 1 is proposed as a technology that utilizes this feeling estimation technology and a technology relevant to photographs, action logs, and the like of a user which are acquired in large amounts. Below Patent Literature 1 discloses a technology that saves biometric information and action information of a photographer at the time of capturing an image, in association with the captured image. Thereby, an important image (an image that is captured in a special psychological state) can be searched for from a huge number of images.

CITATION LIST

Patent Literature

Patent Literature 1: JP 2009-188899A

SUMMARY OF INVENTION

Technical Problem

Here, in these days, a scheme that derives a correlative relationship (a structure) from a large amount of seemingly inorganic data, and a computing power that supports this are becoming real, like a technology referred to as what is called deep learning. Thus, a data group relevant to a large amount of photographs and action logs, and a data group relevant to feelings of that time are analyzed, in order to calculate a correlative relationship of action and feeling.

Then, in an era in which cloud devices (imaging devices that can connect to networks, etc.) build myriad of networks on cloud, if a large amount of action logs and feeling data uploaded from each cloud device can be mapped, creation of a feeling map of the entire global environment and feeling analysis can be enabled. In this case, an action for leading to predetermined feeling can be guided for a user.

However, in the past technology, user guidance according to the feeling map has not been considered at all.

Thus, the present disclosure proposes a communication system, a control method, and a storage medium, which can guide a user to an action for having the predetermined feeling in accordance with a feeling map.

Solution to Problem

According to the present disclosure, there is provided a communication system including: an acquisition unit configured to acquire present position information of a user; a guiding information generation unit configured to generate guiding information in accordance with the present position information and map information in which feeling data is mapped; and a supply unit configured to supply the guiding information to the user.

According to the present disclosure, there is provided a control method including: acquiring present position information of a user from a client; generating guiding information in accordance with the present position information and map information in which feeling data is mapped; and performing control to supply the guiding information to the user.

According to the present disclosure, there is provided a storage medium storing a program that causes a computer to function as: an acquisition unit configured to acquire present position information of a user; a guiding information generation unit configured to generate guiding information in accordance with the present position information and map information in which feeling data is mapped; and a supply unit configured to supply the guiding information to the user.

Advantageous Effects of Invention

As described above, according to the present disclosure, an action for having the predetermined feeling can be guided for a user in accordance with the feeling map.

Note that the effects described above are not necessarily limited, and along with or instead of the effects, any effect that is desired to be introduced in the present specification or other effects that can be expected from the present specification may be exhibited.

DESCRIPTION OF EMBODIMENT(S)

Hereinafter, (a) preferred embodiment(s) of the present disclosure will be described in detail with reference to the appended drawings. In this specification and the drawings, elements that have substantially the same function and structure are denoted with the same reference signs, and repeated explanation is omitted.

Also, description will be made in the following order.
1. Overview of Communication System According to Embodiment of Present Disclosure
2. Basic Configuration
2-1. Exemplary Configuration of Server 2
2-2. Exemplary Configuration of Clients 3 (for Data Collection)
2-3. Exemplary Configuration of Client 1 (for Guiding Information Presentation)
3. Each Navigation
3-1. Navigation According to Feeling Map
3-2. Content Navigation
3-3. Environment Information Navigation
4. Conclusion

Figure 1:
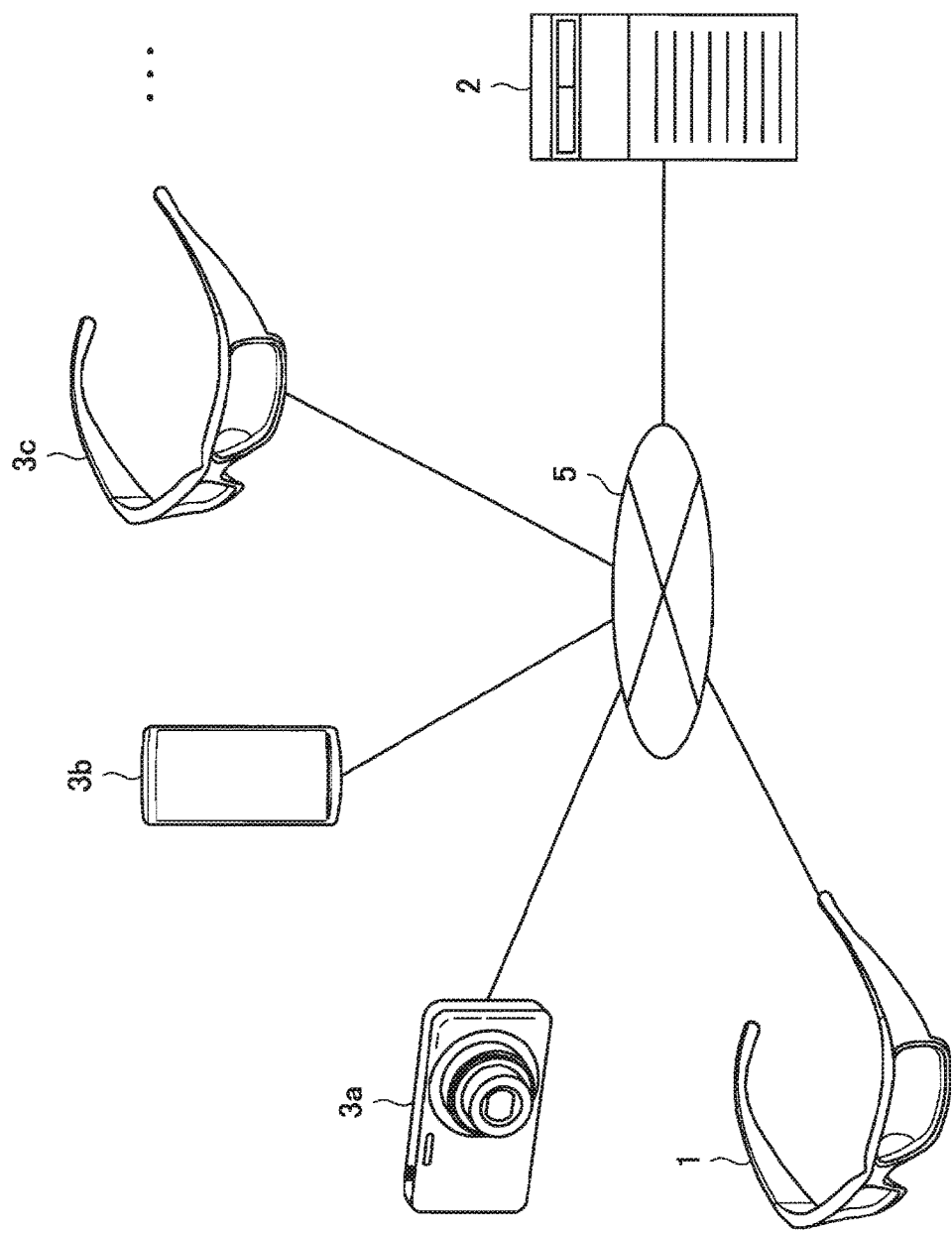
FIG. 1 is a diagram for describing an overview of the communication system according to an embodiment of the present disclosure.

1. Overview of Communication System According to Embodiment of Present Disclosure First, an overview of the communication system according to an embodiment of a present disclosure will be described with reference to FIG. 1. FIG. 1 is a diagram for describing the overview of the communication system according to an embodiment of the present disclosure. As illustrated in FIG. 1, the communication system according to the present embodiment includes data collection clients 3, a server 2, a guiding information presenting client 1.

The data collection clients 3 are information processing terminals, such as a client 3a configured with a camera device, a client 3b configured with a smartphone, a client 3c configured with an eyeglass head mounted display (HMD), for example, as illustrated in FIG. 1. The clients 3a to 3c acquire, and upload to the server 2 via the network 5, data (for example, biometric information, face image, sound, etc.) for estimating feeling of each possessing user, and present position information, viewing content data, surrounding environment information, etc.

The server 2 estimates feeling of the possessing user on the basis of the data for estimating the feeling which is collected from each client 3, and generates data indicating a correlative relationship between the estimated feeling and the position information, content data, and environment information that are collected together. For example, the server 2 generates a feeling map in which estimated feelings are mapped on a map, on the basis of the position information. Also, the server 2 can generate a database (DB) indicating a correlative relationship between the estimated feeling and the content data, and a database indicating a correlative relationship between the estimated feeling and the environment information. Note that, in FIG. 1, only three clients 3a to 3c have been illustrated as examples of the data collection clients 3, but the data collection clients 3 can exist in large numbers on the networks, and the server 2 can collect a large amount of data from a large number of clients 3, to generate a feeling map, a content-feeling DB, and an environment-feeling DB of an area scale, a country scale, or the entire earth scale.

Also, the server 2 generates, and returns to the client 1, guiding information that guides an action (for example, a direction of movement, viewing recommendation of a certain content, a proposal of environment improvement) for leading a user to predetermined feeling on the basis of the feeling map, the content-feeling DB, or the environment-feeling DB, in response to a request from the guiding information presenting client 1.

The guiding information presenting client 1 requests transmission of the guiding information that guides the action for leading the user to the predetermined feeling, to the server 2, and presents the guiding information to the user by outputting a display or sound of the guiding information that is returned from the server 2 in response to the request. For example, the client 1 acquires, and transmits to the server 2, the present position information, viewing content data, and surrounding environment information, and requests transmission of the guiding information. Also, the guiding information presenting client 1 is configured with the eyeglass HMD illustrated in FIG. 1, and can be configured with an output terminal that is connectable to a network, such as a smartphone, a tablet terminal, a mobile phone terminal, a camera device, a game machine, a music player, or the like.

In the above, the overview of the communication system according to an embodiment of the present disclosure has been described. Thereby, the action for evoking the predetermined feeling can be presented to the user, in the present embodiment. For example, the happiness degree map is generated on the basis of the correlative relationship between the happy feeling and the position information, and the route for evoking happy feeling can be guided for the user by using the happiness degree map. Note that, in the example illustrated in FIG. 1, the data collection clients 3 and the guiding information presenting client 1 are illustrated as the separate devices, but may be the same device.

2. Basic Configuration

Next, respective exemplary configurations of the server 2, the client 3, and the client 1 that are included in the communication system according to the present embodiment will be sequentially described with reference to FIGS. 2 to 4.

2-1. Exemplary Configuration of Server 2

Figure 2:
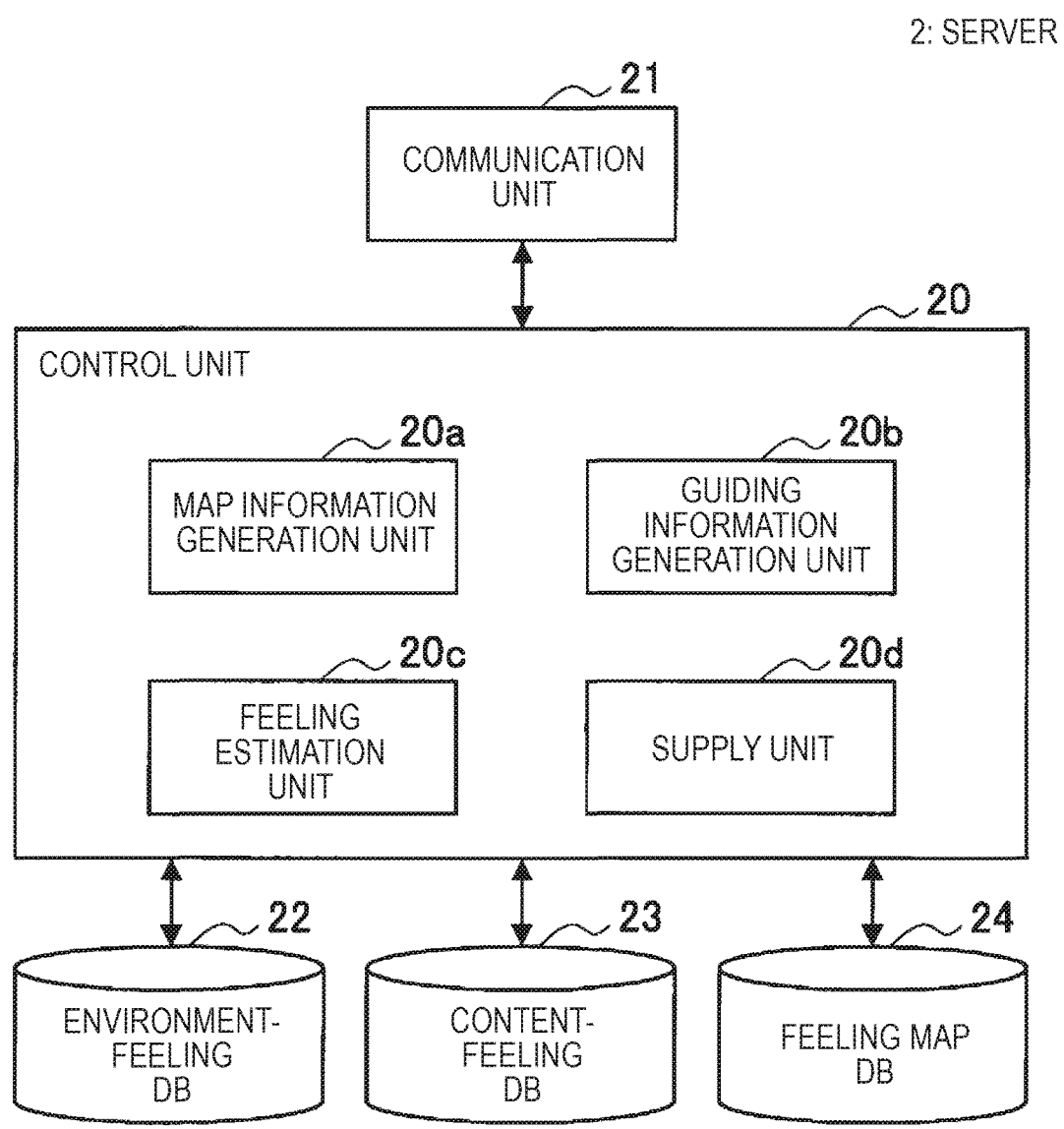
FIG. 2 is a block diagram illustrating an example of a basic configuration of a server according to the present embodiment.

FIG. 2 is a block diagram illustrating an example of a basic configuration of the server 2 according to the present embodiment. As illustrated in FIG. 2, the server 2 includes a control unit 20, a communication unit 21, an environment-feeling DB 22, a content-feeling DB 23, and a feeling map DB 24.

Control Unit

The control unit 20 is configured with a microcomputer that includes a central processing unit (CPU), a read only memory (ROM), a random access memory (RAM), a non-volatile memory, and an interface unit for example, and controls each component of the server 2.

Also, the control unit 20 according to the present embodiment functions as a map information generation unit 20a, a guiding information generation unit 20b, a feeling estimation unit 20c, and a supply unit 20d, as illustrated in FIG. 2. The map information generation unit 20a generates map information that maps the feeling data, and stores the generated map information (also referred to as a feeling map) in the feeling map DB 24. More specifically, the map information generation unit 20a locates the feeling data that is estimated on the basis of the data for estimating the feeling of the user which is transmitted from the clients 3 that performs the data collection, on the map, on the basis of the position information transmitted together. Also, the map information generation unit 20a may generate the map information, by statistically analyzing the correspondence relationship of a large amount of feeling data and the position information which are transmitted from a large number of clients 3.

In the present specification, the data for estimating the feeling of the user is biometric information, such as perspiration, pulse, heartbeat, vibration of body, brain wave, myoelectricity, blood flow change, an captured image that captures a face (expression) of the user, sound, or the like for example. The map information generation unit 20a estimates the feeling of the user on the basis of the values of the biometric information, an analysis result of the captured image, or the like. The feeling is generally defined by any one or a combination of eight basic feeling such as joy, sadness, trust, disgust, risk, anger, surprise, and anticipation. The map information generation unit 20a estimates the degree of happiness (the degree of happiness that the user feels) for example, among these various feelings. More specifically, for example, the map information generation unit 20a can estimate the degree of happiness according to a smile degree, when smile is detected from a face image of the user. Also, the map information generation unit 20a can estimate the degree of happiness on the basis of conversation detail, pitch and intonation of voice, laughter, or the like, by analyzing the sound of the user.

Further, the map information generation unit 20a may generate the feeling map by the attribute of the user. The attribute of the user is age, age period, gender, hobby, preference, place of origin, or like for example.

The estimation of the feeling of the user by the map information generation unit 20a described above may be performed in advance at the clients 3 side. In this case, the user's feeling data that has already been estimated is transmitted from the clients 3.

The guiding information generation unit 20b generates the guiding information that guides the action for leading the user to the predetermined feeling, in response to the request from the client 1 that performs the presentation of the guiding information. More specifically, for example, the guiding information generation unit 20b generates the guiding information for guiding the user to the site (or the route) to which the predetermined feeling is linked, in accordance with the present position information transmitted from the client 1, and the feeling map stored in the feeling map DB 24. The guiding information includes the information that instructs, to the user, a direction of movement toward the site (or the route) to which the predetermined feeling is linked.

Also, the guiding information generation unit 20b generates recommendation information of the content data, improvement idea of the environment information, or the like, for leading the user to the predetermined feeling, in accordance with the user's present feeling estimated by the feeling estimation unit 20c described next on the basis of the content data that the user views at the present moment or the environment information surrounding the user. For example, the guiding information generation unit 20b generates the guiding information for guiding (recommending), to the user, the content to which the predetermined feeling is linked, by using the data stored in the content-feeling DB 23. Specifically, for example, when the music that the user listens to at the present moment evokes sad feeling, the guiding information generation unit 20b generates the guiding information that guides the content data (the photograph, the video, the music, etc.) for having joyful happy feeling that is opposite to the sad feeling. Alternatively, the guiding information generation unit 20b generates the guiding information for guiding the user to the improvement to the environment information to which the predetermined feeling is linked, by using the data stored in the environment-feeling DB 22. Specifically, for example, when the present surrounding environment information of the user evokes gloomy feeling, the supply unit 20d generates the guiding information that guides an environment improvement plan (open a window, play the music, light up a room etc.) for having brisk happy feeling that is opposite to the gloomy feeling.

The guiding information generation unit 20b outputs the generated guiding information to the supply unit 20d.

The feeling estimation unit 20c has a function (a first, a second feeling estimation unit) for estimating the present feeling of the user, on the basis of the content data that the user is viewing or the environment information around the user which are transmitted from the client 1 that performs the presentation of the guiding information. Here, the content data that the user is viewing is identification information or feature value of photograph, video, music, or the like, for example. Also, the environment information around the user is time, position, air pressure, air temperature, degree of humidity, an object that exists around, a state of the object, or the like, for example.

The feeling estimation unit 20c extracts the feeling data which is linked to the content data that is the same as or similar to the content data that the user is viewing at the present moment, on the basis of the data (learning result) indicating the correlative relationship between the content data and the feeling data, which is stored in the content-feeling DB 23, and estimates the extracted feeling data as the present feeling of the user. Also, the feeling estimation unit 20c extracts the feeling data that is linked to the environment information that is the same as or similar to the present surrounding environment information of the user, on the basis of the data (learning result) indicating the correlative relationship between the environment information and the feeling data, which is stored in the environment-feeling DB 22, and estimates the extracted feeling data as the present feeling of the user.

The feeling estimation unit 20c outputs the user's present feeling data that is estimated on the basis of the content data or the environment information, to the guiding information generation unit 20b.

The supply unit 20d performs control to supply, to the user, the guiding information that guides the user to the action for having the predetermined feeling which is generated by the guiding information generation unit 20b. That is, the supply unit 20d performs control to transmit the guiding information generated by the guiding information generation unit 20b, to the client 1 from the communication unit 21, and causes the client 1 to present (output a display of or output sound of) the guiding information to the user.

For example, the supply unit 20d performs control to supply, to the user, the guiding information that instructs the direction of movement to the site or the route to which the predetermined feeling is linked, a map image indicating the distribution of the predetermined feeling degree of the area around the present position of the user, or the like.

Also, the supply unit 20d may perform control to supply, to the user, the recommendation information of the content data to which the predetermined feeling is linked.

Also, the supply unit 20d may perform control to supply, to the user, the information that proposes improvement into the environment to which the predetermined feeling is linked.

Communication Unit

The communication unit 21 connects with the network 5, and performs transmission and reception of the data with the clients 1, 3. For example the communication unit 21 receives (acquires) data for estimating the feeling of the user, the position information, the content data, and the environment information, from the clients 3 that performs data collection. Also, the communication unit 21 receives (acquires) the present position information from the client 1 that performs the presentation of the guiding information, and in response to this, returns the guiding information in accordance with the control by the supply unit 20d.

Environment-Feeling DB

The environment-feeling DB 22 stores the data indicating the correlative relationship between the environment information (the time, the position, the air pressure, the air temperature, the degree of humidity, the position, the object, the state of the object, etc.) and the feeling data. For example, a learning result that is learned by statistically analyzing the correlative relationship of the environment information and the feeling data transmitted in large amounts from the large number of data collection clients 3 is stored in the environment-feeling DB 22.

Content-Feeling DB

The content-feeling DB 23 stores data indicating the correlative relationship between the content data and the feeling data. For example, a learning result that is learned by statistically analyzing the correlative relationship of the content data and the feeling data transmitted in large amounts from a large number of data collection clients 3 is stored in the content-feeling DB 23.

Feeling Map DB

The feeling map DB 24 stores the feeling map generated by the map information generation unit 20a.

2-2. Exemplary Configuration of Clients 3 (For Data Collection)

Next, the configuration of the data collection clients 3 will be described with reference to FIG. 3. FIG. 3 is a block diagram illustrating an inner configuration an example of the client 3a (camera device) according to the present embodiment. FIG. 3 illustrates the configuration of the client 3a configured with the camera device, as an example of the client 3.

Figure 3:
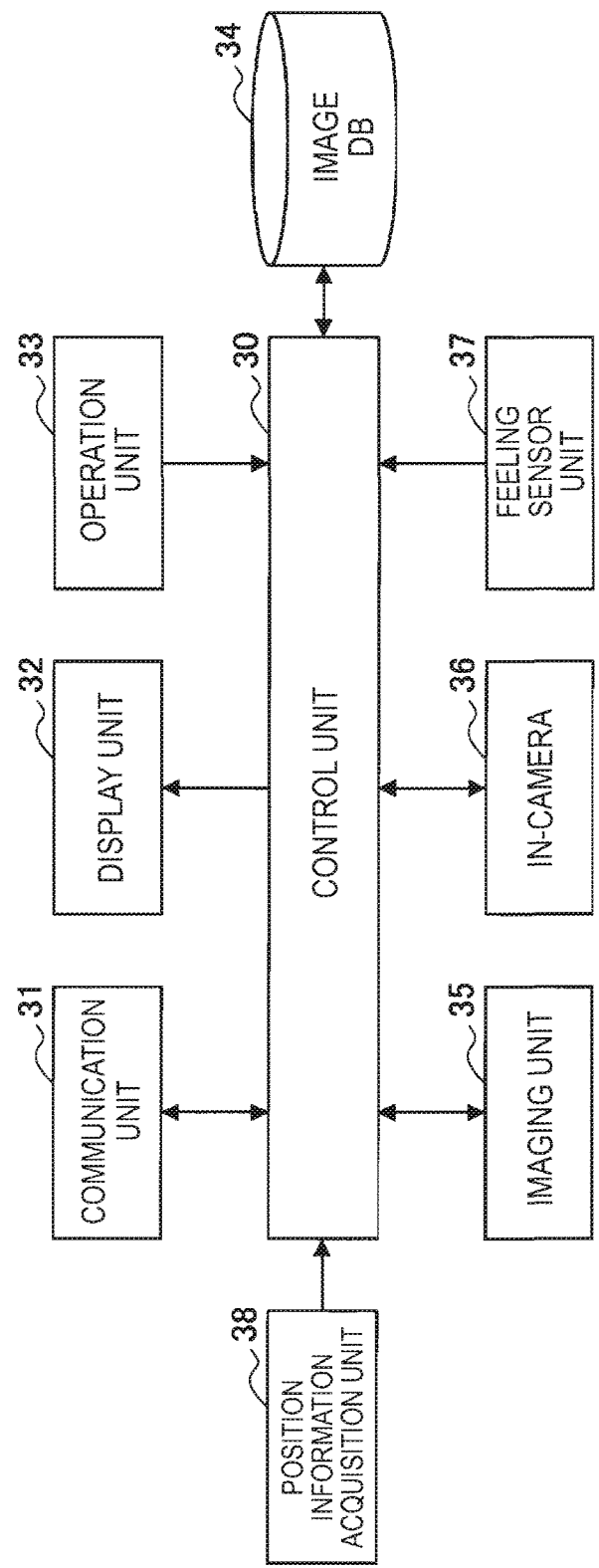
FIG. 3 is a block diagram illustrating an example of an inner configuration of a client that performs data collection according to the present embodiment.

As illustrated in FIG. 3, the client 3a (the camera device) includes a control unit 30, a communication unit 31, a display unit 32, an operation unit 33, an image DB 34, an imaging unit 35, an in-camera 36, a feeling sensor unit 37, and a position information acquisition unit 38.

Control Unit

The control unit 30 is configured with a microcomputer that includes a CPU, a ROM, a RAM, a non-volatile memory, and an interface unit for example, and controls each component of the client 3a. Specifically, for example, the control unit 30 controls and instructs the imaging unit 35 to execute the image capturing when pressing of the shutter button is detected by the operation unit 33. Also, the control unit 30 executes control to capture an image of the face (the expression) of the user (photographer) by the in-camera 36, when executing the image capturing by the imaging unit 35, and executes control to transmit the face image that is captured by the in-camera 36 from the communication unit 31 to the server 2 as the data for estimating the feeling of the user. Alternatively, when executing the image capturing by the imaging unit 35, the control unit 30 executes control to transmit sensor values (biometric information such as perspiration, pulse, or body temperature) that are detected by the feeling sensor unit 37 provided in the shutter button or the like, as the data for estimating the feeling of the user, from the communication unit 31 to the server 2, for example. Further, when transmitting, to the server 2, the data for estimating the feeling of the user, such as face image, biometric information, and the like, the control unit 30 executes control to transmit the present position information acquired by the position information acquisition unit 38, or the captured image (the subject image) captured by the imaging unit 35 together.

As described above, in the present embodiment, the data collection clients 3 transmits the data (the face image, the biometric information, etc.) for estimating the feeling of the user, to the server 2, together with the present position information, and thereby the server 2 side performs the feeling estimation of the user, and the association between the estimated feeling and the position information (the generation of the feeling map). Also, the data collection clients 3 transmits the data (the face image, the biometric information, etc.) for estimating the feeling of the user, to the server 2, together with the captured image (the subject image), and thereby the server 2 side performs the feeling estimation of the user, and the association between the estimated feeling and the captured image (the generation and the learning of the content-feeling DB).

Communication Unit

The communication unit 31 connects with the network 5, and performs transmission and reception of the data, with the server 2.

Display Unit

The display unit 32 has a function for displaying characters, images, and other information on a display screen image, in accordance with the control of the control unit 30.

The display unit 32 is configured with a liquid crystal display, an organic EL display, or a like, for example.

Operation Unit

The operation unit 33 detects the operation by the user, and has a function for outputting the detected user operation to the control unit 30. The operation unit 33 is configured with a physical structure such as a shutter button, a power supply button, and a zoom button, for example, and may be configured with an operation surface (for example, a touch panel) that is superimposed on the display screen image and detects a contact position of the user to the display screen image.

Image DB

The image DB 34 stores the captured image captured by the imaging unit 35, and the face image captured by the in-camera 36.

Imaging Unit

The imaging unit 35 includes a lens system configured with an image capturing lens, a diaphragm, a zoom lens, and a focus lens, a drive system that causes a lens system to perform focus operation and zoom operation, a solid-state image sensor array that generates an image capturing signal by photoelectrically converting a captured image light obtained by the lens system, etc. The solid-state image sensor array may be configured with a charge coupled device (CCD) sensor array or a complementary metal oxide semiconductor (CMOS) sensor array, for example.

The imaging unit 35 executes the image capturing in accordance with an image capturing execution instruction by the control unit 30. The image captured by the imaging unit 35 is stored in the image DB 34.

In-Camera

The in-camera 36 is an imaging unit provided toward the user side, to capture an image of the user who is a photographer (an operator). Specifically, for example, the in-camera 36 is provided with its inside as the image capturing direction, on the surface of the opposite side to the surface on which the image capturing lens of the imaging unit 35, in which the outside of the camera device (the client 3a) is the image capturing direction, is provided.

The in-camera 36 captures an image of the face of the user that performs the image capturing, in accordance with the control by the control unit 30. The face image captured by the in-camera 36 is output to the control unit 30, and is transmitted to the server 2 as the data for estimating the feeling of the user, in accordance with the control of the control unit 30.

Feeling Sensor Unit

The feeling sensor unit 37 is various types of sensors that detect biometric information such as the pulse, the perspiration, or the body temperature of the user, as the data for estimating the feeling of the user who is the operator of the camera device (the client 3a). The feeling sensor unit 37 is provided in the shutter button or the operation surface for example, and can detect the biometric information when the user presses the shutter button or touches the operation surface to perform the image capturing operation. The feeling sensor unit 37 outputs the detected biometric information to the control unit 30, and is transmitted to the server 2 as the data for estimating the feeling of the user by the control unit 30.

Position Information Acquisition Unit

The position information acquisition unit 38 has a function for detecting the present position of the client 3a on the basis of a signal acquired from the outside. Specifically, the position information acquisition unit 38 is configured with a global positioning system (GPS) positioning unit for example, and receives the radio wave from the GPS satellites, and detects the position at which the client 3a exists, and outputs the detected position information to the control unit 30. Also, the position information acquisition unit 38 may detect the position by transmission and reception, short range communication or the like, with Wi-Fi (registered trademark), mobile phone, PHS, smartphone, or the like for example, in addition to the GPS.

In the above, the configuration of the client 3a configured with the camera device has been described as an exemplary configuration of the data collection clients 3. However, the configuration of the clients 3 according to the present embodiment is not limited to the example illustrated in FIG. 3, but for example the clients 3 may include the environment information acquisition unit that further acquires the surrounding environment information.

The environment information acquisition unit has a function for sensing the air temperature, the degree of humidity, the intensity of illumination, the weather information, the object that exists around, the state of the object, or the like for example, as the surrounding environment information (the field information). For example, the environment information acquisition unit is configured with a humidity sensor, an illuminance sensor, a temperature sensor, or the like. Also, the environment information acquisition unit may extract the object that exists around, the state of the object, or the like, as the environment information, on the basis of the subject image acquired by the imaging unit 35.

The environment information acquired by the environment information acquisition unit is transmitted to the server 2, together with the data (face image, biometric information, etc.) for estimating the feeling of the user. As described above, in the present embodiment, the data collection clients 3 transmits the environment information to the server 2 together with the data (the face image, the biometric information, etc.) for estimating the feeling of the user, so that the server 2 side performs the feeling estimation of the user, and the association between the estimated feeling and the environment information (the generation and the learning of the environment-feeling DB).

2-3. Exemplary Configuration of Client 1 (For Guiding Information Presentation)

Next, the configuration of the guiding information presenting client 1 will be described. The client 1 is configured with the eyeglass HMD for example, as illustrated in FIG. 1. The eyeglass HMD is an eyeglass wearable device worn on the user, and has a configuration in which a pair of display units for the left eye and for the right eye are located at immediately in front of the both eyes of the user, that is, at the site at which the lenses of a normal eyeglasses position, in the wearing state. The display unit is transmissive, and the display unit is in a through state, that is, a transparent or translucent state, and thus there is no trouble in the normal life of the user even if the eyeglass HMD is always worn.

Figure 4:
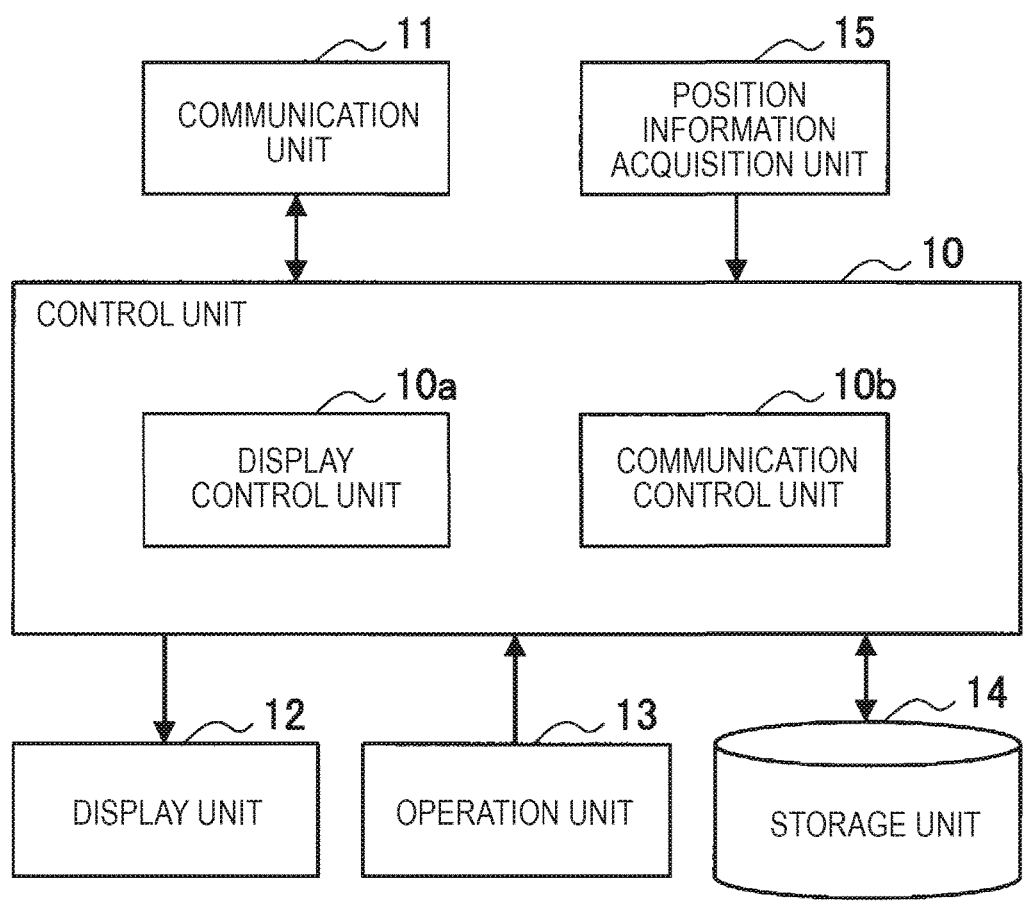
FIG. 4 is a block diagram illustrating an example of an inner configuration of a client that performs presentation of guiding information according to the present embodiment.

Here, an example of the inner configuration of the client 1 when configured with the eyeglass HMD is illustrated in FIG. 4. The client 1 includes a control unit 10, a communication unit 11, a display unit 12, an operation unit 13, a storage unit 14, and a position information acquisition unit 15, as illustrated in FIG. 4.

Control Unit

The control unit 10 is configured with a microcomputer that includes a CPU, a ROM, a RAM, a non-volatile memory, and an interface unit for example, and controls each component of the client 1. Also, the control unit 10 according to the present embodiment functions as a display control unit 10a and a communication control unit 10b, as illustrated in FIG. 4.

The display control unit 10a performs generation of the screen image that is displayed on the display unit 12, and display control. For example, the display control unit 10a executes control to display on the display unit 12 the guiding information that is received from the server 2 by the communication unit 11. Also, the display control unit 10a can control the transmittance of the display unit 12.

The communication control unit 10b controls data transmission from the communication unit 11. The communication control unit 10b transmits the present position information acquired by the position information acquisition unit 15 from the communication unit 11 to the server 2 for example, and requests the feeling navigation that leads the user to the predetermined feeling, to the server 2. In response to such a request, the server 2 side generates the guiding information for guiding the user to the site and the route in which the predetermined feeling is associated on the basis of the present position information of the user and the feeling map, and returns the generated guiding information to the client 1.

Communication Unit

The communication unit 11 connects with the network 5, and includes a function for performing communication with the server 2. For example, the communication unit 11 transmits, to the server 2, the present position information and a request of the feeling navigation, in accordance with the control of the communication control unit 10b. Also, the communication unit 11 receives the guiding information returned from the server 2 in response to the request of the feeling navigation.

Display Unit

As described above, the display unit 12 is located immediately in front of the both eyes of the user, that is, at the site at which the lenses of the normal eyeglasses position, in a state in which the user wears the client 1 (the eyeglass HMD). A liquid crystal panel is used for this display unit 12 for example, and the transmissivity of the liquid crystal panel is controlled by the display control unit 10a, so that the display unit 12 becomes a through state, that is, a transparent or translucent state.

Also, the display unit 12 according to the present embodiment displays the guiding information transmitted from the server 2, in accordance with the control by the display control unit 10a. A specific exemplary display of the guiding information will be described later with reference to FIGS. 8 and 9. Also, the display unit 12 can reproduce content such as photograph and video, in accordance with the control by the display control unit 10a.

Operation Unit

The operation unit 13 has a function for detecting the user operation, and outputs the detected user operation to the control unit 10. The operation unit 13 may be configured with a physical structure such as a power supply switch, or with a detection unit that detects tap operation (or vibration) to the client 1 (the eyeglass HMD) main body. Also, the operation unit 13 may recognize a gesture input by capturing an image of the gesture of the user by the camera provided toward the outside, and may recognize a sight line input by capturing an image of the eye of the user by the camera provided toward the inside. Alternatively, the operation unit 13 may recognize an audio input by acquiring the sound of the user by a microphone that collects the ambient sound.

Storage Unit

The storage unit 14 stores a program for executing various types of processing by the control unit 10.

Position Information Acquisition Unit

The position information acquisition unit 15 has a function for detecting the present position of the client 1 on the basis of the signal acquired from the outside. The position information acquisition unit 15 outputs the acquired present position information to the control unit 10.

In the above, the configuration of the client 1 configured with the eyeglass HMD has been described as an exemplary configuration of the guiding information presenting client 1. However, the configuration of the client 1 according to the present embodiment is not limited to the example illustrated in FIG. 4, but for example, the client 1 may further include a sound reproduction unit (a speaker).

The sound reproduction unit is configured with a pair of earphone speakers that can be inserted into the right earhole and the left earhole of the user (or one earphone speaker that can be inserted into only one of ears), in the wearing state of the client 1 (the eyeglass HMD) for example. Also, the sound reproduction unit outputs the sound of the guiding information transmitted from the server 2, in accordance with the control of the control unit 10, and reproduces the content data such as music.

Also, the client 1 may further include an environment information acquisition unit. The environment information acquisition unit has a function for sensing the air temperature, the degree of humidity, the intensity of illumination, the weather information of the present position, the object that exists around, the state of the object, or the like for example, as the surrounding environment information (the field information).

Also, the communication control unit 10b according to the present embodiment may transmit, to the server 2, the content data of the content (photograph, video, music, etc.) that the user views at the present moment or the present surrounding environment information, and request the transmission of the guiding information for leading the user to the predetermined feeling. For example, when the content data is transmitted, the server 2 side generates the guiding information that recommends another content that leads the user to the predetermined feeling in response to the present feeling of the user which is estimated on the basis of the content data, and returns the generated guiding information to the client 1. Also, when the environment information is transmitted, the server 2 side generates the guiding information that proposes improvement to another environment information that leads the user to the predetermined feeling in response to the present feeling of the user which is estimated on the basis of the environment information, and returns the generated guiding information to the client 1.

In the above, each component of the server 2, the data collection client 3, and the guiding information presenting client 1 which are included in the communication system according to the present embodiment has been described specifically. Note that the data collection client 3 and the guiding information presenting client 1 may be the same device, as described above.

Next, each navigation executed by the communication system according to an embodiment of the present disclosure will be described specifically with a plurality of examples.

3. Each Navigation

3-1. Navigation According to Feeling Map

First, navigation according to the feeling map will be described with reference to FIGS. 5 to 9.

3-1-1. Data Collection

Figure 5:
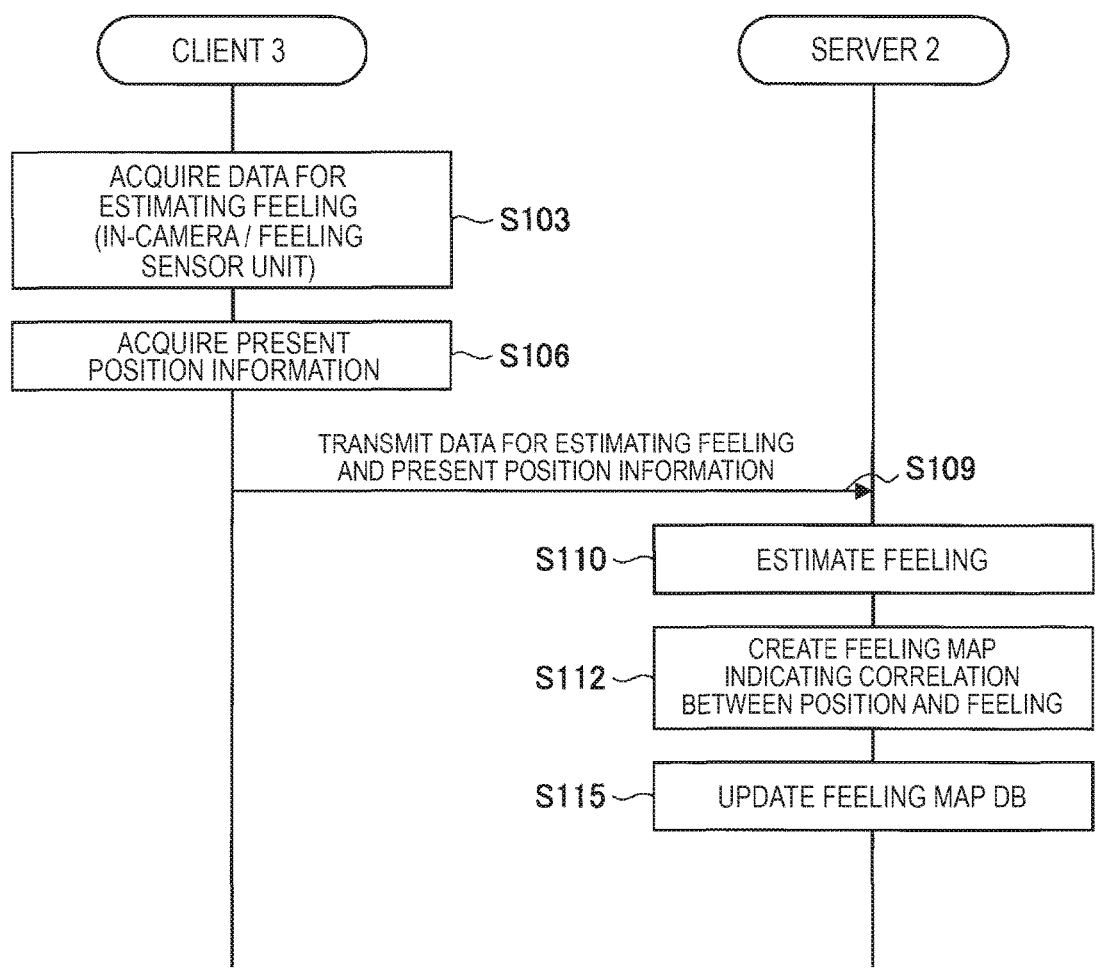
FIG. 5 is a sequence diagram illustrating an operation process at the time of feeling map generation.

FIG. 5 is a sequence diagram illustrating an operation process at the time of feeling map generation. As illustrated in FIG. 5, the clients 3 first acquires the data for estimating the feeling of the user, in step S103. Specifically, in the case of the client 3a (refer to FIG. 3), the data is acquired by the image capturing of the face image by the in-camera 36, or the detection of the biometric information by the feeling sensor unit 37, for example.

Thereafter, the clients 3 acquires the present position information, in step S106.

Thereafter, the clients 3 transmits the data for estimating the feeling, and the present position information, to the server 2, in step S109.

Subsequently, the map information generation unit 20a of the server 2 estimates the feeling of the user, on the basis of the data (the face image and the biometric information) for estimating the received feeling, in step S110. Note that the feeling estimation of the user may be performed at the clients 3 side, and in this case the feeling that is estimated already is transmitted to the server 2, and thus S110 is omitted.

Thereafter, the map information generation unit 20a creates the feeling map indicating the correlation between the position and the feeling, in step S112. That is, the map information generation unit 20a associates (maps) the estimated feeling, with the position on the map indicated by the present position information.

Thereafter, in step S115, the map information generation unit 20a stores the generated feeling map in the feeling map DB 24, and updates the database of the feeling map. Steps S103 to S115 described above are performed repeatedly, and the map information generation unit 20a continues updating the database of the feeling map, on the basis of the position information and feeling data transmitted from each client 3 continually. In the present embodiment, the feeling map indicating what feeling is evoked in which site and area can be generated more accurately, by statistically analyzing a large amount of position information and feeling data that are collected continually from the myriad of clients 3 that are connected via the network 5.

3-1-2. Navigation

Next, the navigation according to the generated feeling map will be described with reference to FIGS. 6 to 9. The type of the navigation is various, but here, for example, a case in which the route navigation from the present position to the destination place and the route navigation around the present position are performed in accordance with the feeling map will be described. Also, the feeling map that is used in the navigation uses the feeling map (also referred to as a happiness map) indicating the correlative relationship of the degree of happiness and the position, as an example. Thereby, the happiness navigation is achieved in the present embodiment.

Navigation 1

Figure 6:
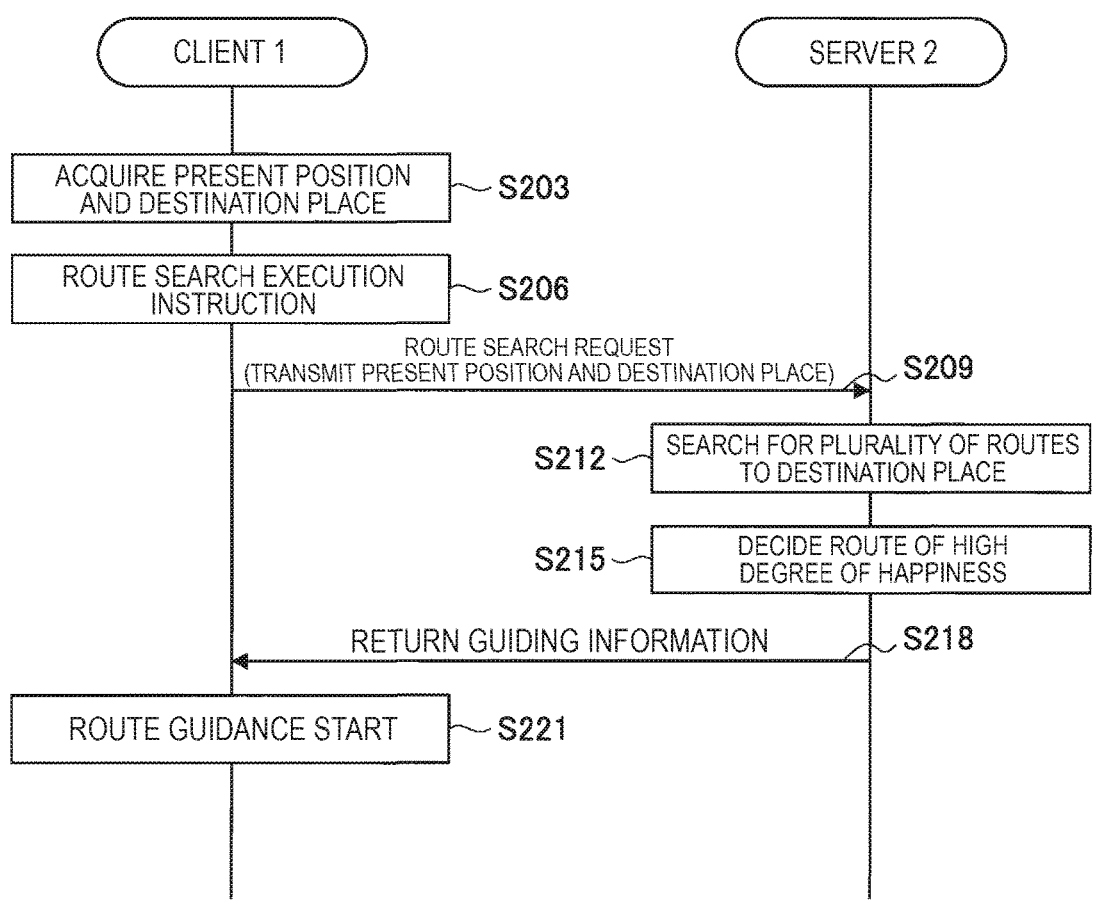
FIG. 6 is a sequence diagram illustrating an operation process of a navigation according to a feeling map.

First, as the navigation 1, a case in which the route navigation from the present position to the destination place is performed in accordance with the feeling map will be described with reference to FIG. 6. FIG. 6 is a sequence diagram illustrating an operation process of the navigation according to the feeling map. As illustrated in FIG. 6, the client 1 first acquires the information of the present position and the destination place, in step S203. The client 1 acquires the present position information by the position information acquisition unit 38, and acquires the destination place by gesture input, audio input, or tap operation, for example.

Thereafter, the client 1 recognizes the route search execution instruction, in step S206. The route search execution instruction is performed by gesture input, audio input, or tap operation by the user, for example.

Thereafter, in step S209, the client 1 transmits the information of the present position and the destination place to the server 2 and performs the route search request to the destination place.

Subsequently, in step S212, the guiding information generation unit 20b of the server 2 searches for a plurality of routes to the destination place, on the basis of the information of the received present position and the destination place.

Thereafter, in step S215, the guiding information generation unit 20b decides the route via the site and the area in which the degree of happiness is high, among a plurality of searched routes, with reference to the plurality of searched routes and the happiness map stored in the feeling map DB 24, and generates the guiding information to the destination place.

Thereafter, in step S218, the supply unit 20d executes control to transmit the guiding information generated by the guiding information generation unit 20b from the communication unit 21 to the client 1.

Then, in step S221, the client 1 presents the received guiding information, and starts the route guidance. Specifically, for example, the client 1 may perform the route guidance by superimposing displaying an arrow image indicating the direction of movement based on the guiding information, on the scenery of the real space in the display unit 12.

Thereby, in the present embodiment, the navigation via the site of a high degree of happiness can be performed. Specifically, for example, the navigation via a site of beautiful scenery, a safe road, a road that circumvents a sloping road, a sightseeing spot, or the like is performed, and the user has happy (amused, joyful) feeling. Also, when the navigation according to the happiness map according to the user attribute is performed, for example a child accompanying attribute can be guided to the destination place via the facility or the like where a child can play, such as a park and a library, and a children's hall.

Also, here only the happiness map is used as an example, but the present embodiment is not limited thereto, and can generate the guiding information that avoids the route of anger and guides to the happy route by using a plurality of feeling maps, for example a happiness map and an anger map.

Navigation 2

Figure 7:
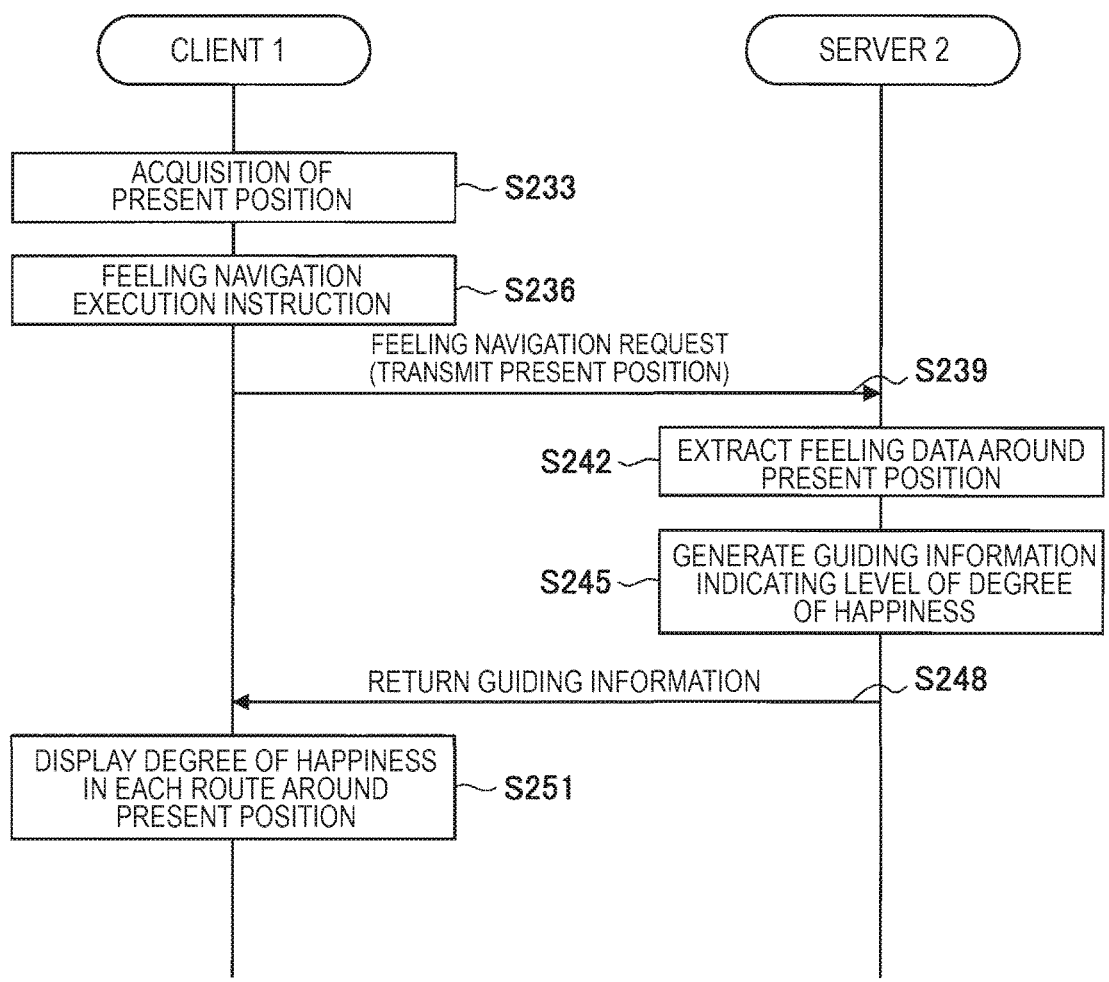
FIG. 7 is a sequence diagram illustrating an operation process of another navigation example according to a feeling map.

Next, as the navigation 2, a case in which the route navigation around the present position is performed in accordance with the feeling map will be described with reference to FIG. 7. FIG. 7 is a sequence diagram illustrating an operation process of another navigation example according to the feeling map. As illustrated in FIG. 7, the client 1 first acquires the information of the present position, in step S233. The client 1 acquires the present position information by the position information acquisition unit 38 for example.

Thereafter, the client 1 recognizes a feeling navigation execution instruction, in step S236. The feeling navigation execution instruction is performed by gesture input, audio input, or tap operation by the user, for example.

Thereafter, in step S239, the client 1 transmits the information of the present position to the server 2, and requests the feeling navigation.

Subsequently, the guiding information generation unit 20b of the server extracts the feeling data around the received present position from the feeling map, in step S242. Here, the level of the degree of happiness around the present position is extracted from the happiness map as an example.

Thereafter, the guiding information generation unit 20b generates the guiding information indicating the level of the degree of happiness around the present position, in step S245.

Thereafter, in step S248, the supply unit 20d executes control to transmit the guiding information generated by the guiding information generation unit 20b from the communication unit 21 to the client 1.

Then, in step S251, the client 1 presents the received guiding information, and displays the degree of happiness in each route around the present position. Here, an example of the display method of the degree of happiness in each route around the present position will be described with reference to FIGS. 8 and 9.

Figure 8:
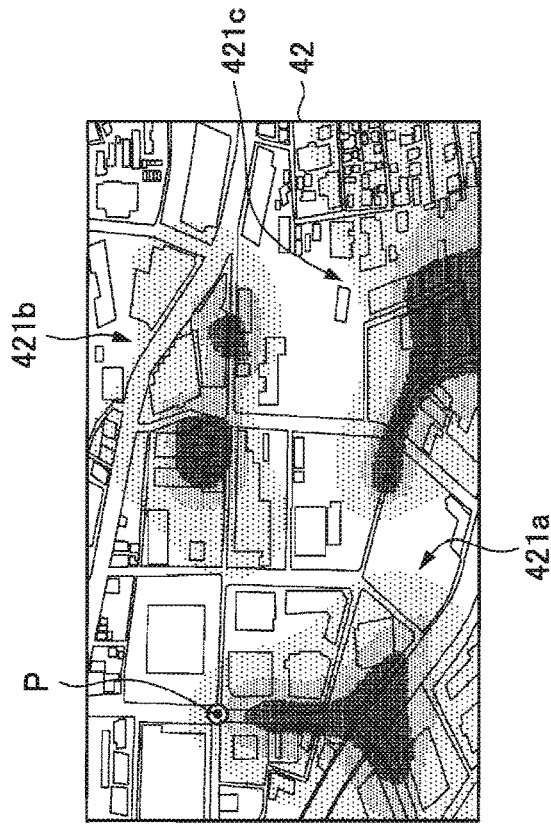
FIG. 8 is a diagram illustrating an exemplary display method of a degree of happiness in each route around a present position.
Figure 8:
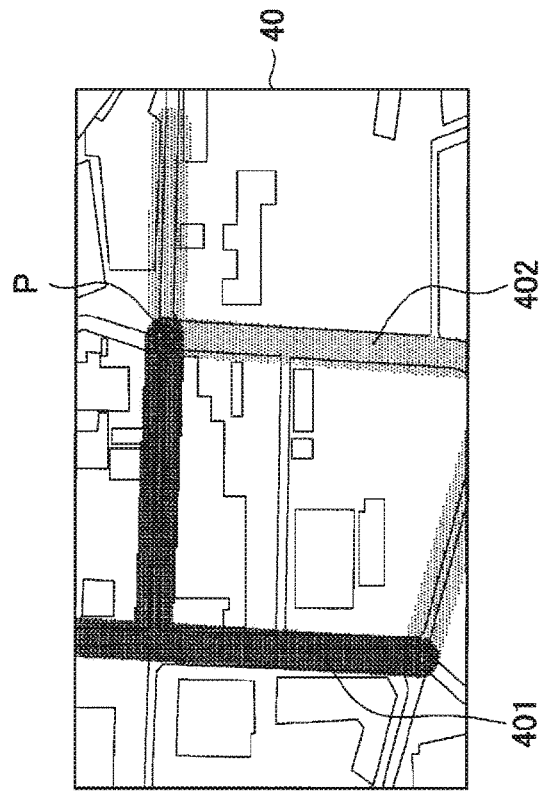
Figure 9:
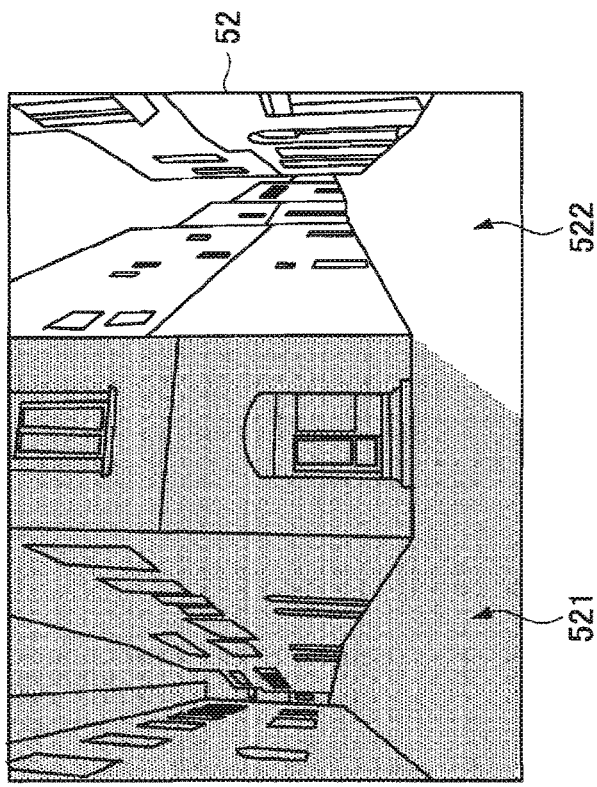
FIG. 9 is a diagram illustrating an exemplary display method of a degree of happiness in each route around a present position.
Figure 9:
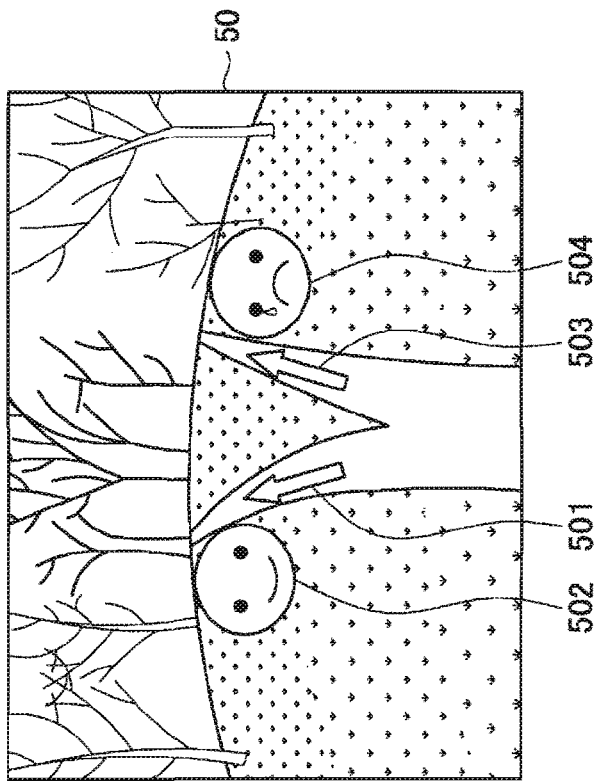

FIGS. 8 and 9 are diagrams illustrating exemplary display methods of the degree of happiness in each route around the present position. In an exemplary display 1 illustrated in FIG. 8 left, a mark P representing the present position and color images 401, 402 representing the degree of happiness in the route around the present position are superimposed and displayed in a map image 40 around the present position. As an example, the deeper color image 401 indicates that the degree of happiness is high, and the lighter color image 402 indicates that the degree of happiness is low, so that the user can intuitively understand the road of a high degree of happiness.

Also, in an exemplary display 2 illustrated in FIG. 8 right, the mark P representing the present position, and distribution images 421a to 421c representing the degree of happiness in the site and the area around the present moment are superimposed and displayed in the map image 42 around the present position. As an example, a region having a deeper color in each distribution image indicates a higher degree of happiness, so that the user can intuitively understand the site where the degree of happiness is high.

The above images of the exemplary display 1 and the exemplary display 2 illustrated in above FIG. 8 are displayed on a part of the display unit 12 for which transmittance is controlled, when the client 1 is the eyeglass HMD for example.

Also, in an exemplary display 3 illustrated in FIG. 9 left, arrow images 501, 503 representing the direction of movement, and expression images 502, 504 according to the feeling data of the movement direction destination are superimposed and displayed in the video 50 of the real space. Thereby, the user can intuitively understand being able to go to the site and the area that makes the happy feeling when proceeding to the left road along the arrow image 501 with which the expression image 502 of the smile is associated, and intuitively understand going to the site and the area that makes the sad feeling when proceeding to the right road along the arrow image 503 with which the expression image 50 of the crying face 4 is associated.

Also, in an exemplary display 4 illustrated in FIG. 9 right, a direction 521 of a low degree of happiness is processed into a dark display in the video 50 of the real space, and a direction 522 of a high degree of happiness is processed into a bright display, in order to navigate the user to proceed to the brighter road naturally.

When the client 1 is the eyeglass HMD for example, the images of the exemplary displays 3, 4 illustrated in the above FIG. 9 may be displayed on a part of the display unit 12 for which transmittance is controlled, and the arrow image 501 or the like may be superimposed and displayed on the scenery of the real space (corresponding to the videos 50, 52 of the real space) that can be visually confirmed via the display unit 12 for which transmittance is controlled.

3-2. Content Navigation

Next, navigation (proposal) of content will be described with reference to FIGS. 10 to 12.

3-2-1. Data Collection

Figure 10:
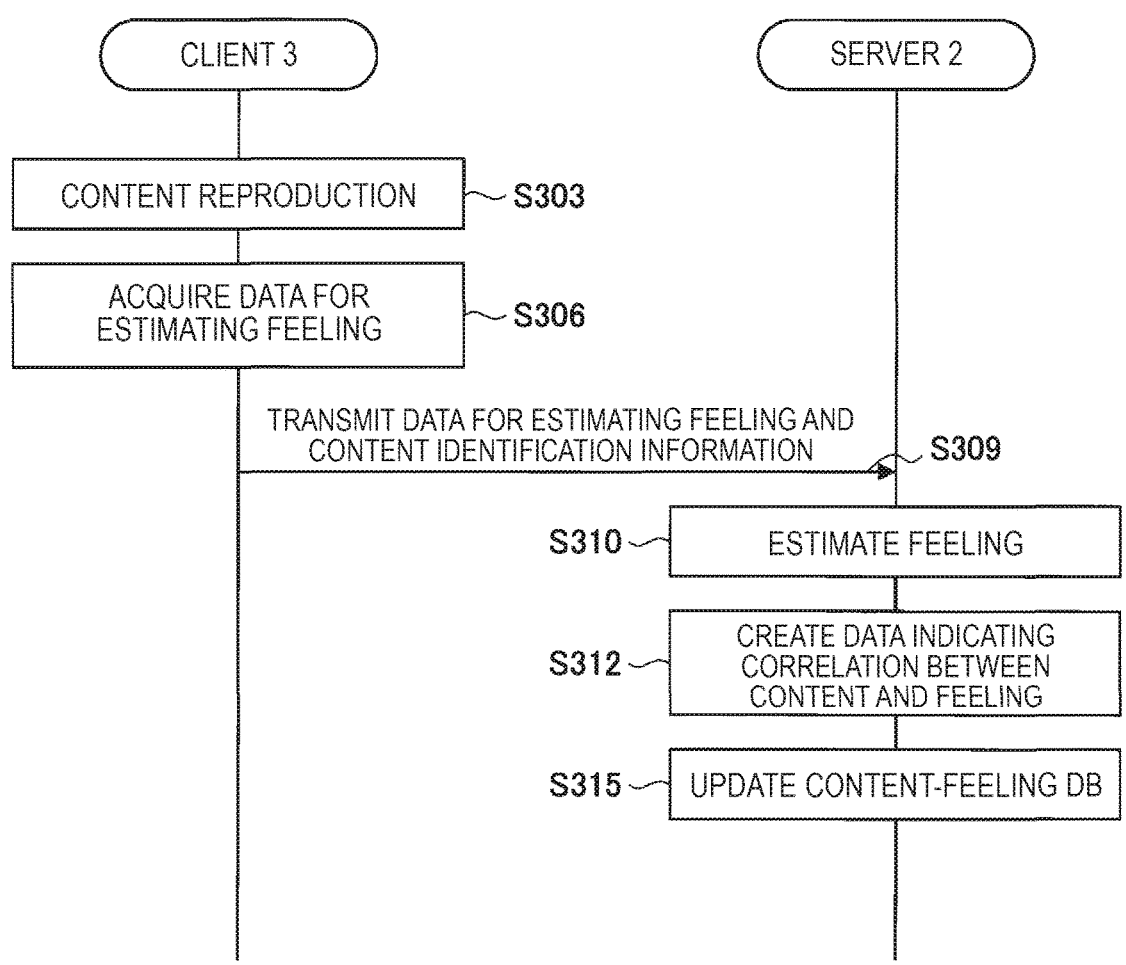
FIG. 10 is a sequence diagram illustrating an operation process at e time of data creation of a content-feeling DB.

FIG. 10 is a sequence diagram illustrating an operation process at the time of data creation of the content-feeling DB 23. As illustrated in FIG. 10, first, in step S303, the data collection clients 3 performs the reproduction of content data such as photograph, video, and music. The reproduction of the content data may be executed in response to user operation. Here, the clients 3 may be the client 3b configured with the smartphone illustrated in FIG. 1. The client 3b performs the reproduction of the content data by using the display unit and the audio output unit.

Thereafter, the clients 3 acquires the data for estimating the feeling of the user, in step S306. Specifically, for example, in the case of the client 3b, the acquisition is performed by a feeling sensor unit that contacts with a hand of the user that holds a client 3b and detects perspiration, temperature, pulse, or the like of the user, and an in-camera provided toward inside to capture an image of the face of the user who browses photographs and videos.

Thereafter, the clients 3 transmits the data for estimating the feeling, and reproduced content information (content data metadata etc. to the server 2, in step S309.

Subsequently, the control unit 20 of the server 2 estimates the feeling of the user, on the basis of the received data (the face image and the biometric information) for estimating the feeling, in step S310. Note that the feeling estimation of the user may be performed at the clients 3 side, and in this case the feeling that is estimated already is transmitted to the server 2, and thus S310 is omitted.

Thereafter, the control unit 20 creates data indicating the correlation between the content and the feeling, in step S312. That is, the control unit 20 learns what feeling the user has when viewing what content.

Thereafter, in step S315, the control unit 20 stores the generated data (the learning result) in the content-feeling DB 23, and updates the database. Steps S303 to S315 described above are performed repeatedly, and the control unit 20 continues updating the content-feeling DB 23, on the basis of the content information and the feeling data transmitted from each client 3 continually. In the present embodiment, the data indicating what content is viewed to evoke what feeling can be generated more accurately, by statistically analyzing a large amount of content information and feeling data that are collected continually from the myriad of clients 3 that are connected via the network 5.

3-2-2. Navigation

Next, navigation that uses the data of the generated content-feeling DB 23 will be described with reference to FIGS. 11 to 12. In the content navigation according to the present embodiment, the content for leading the user to the predetermined feeling is supplied (guided) to the user.

Figure 11:
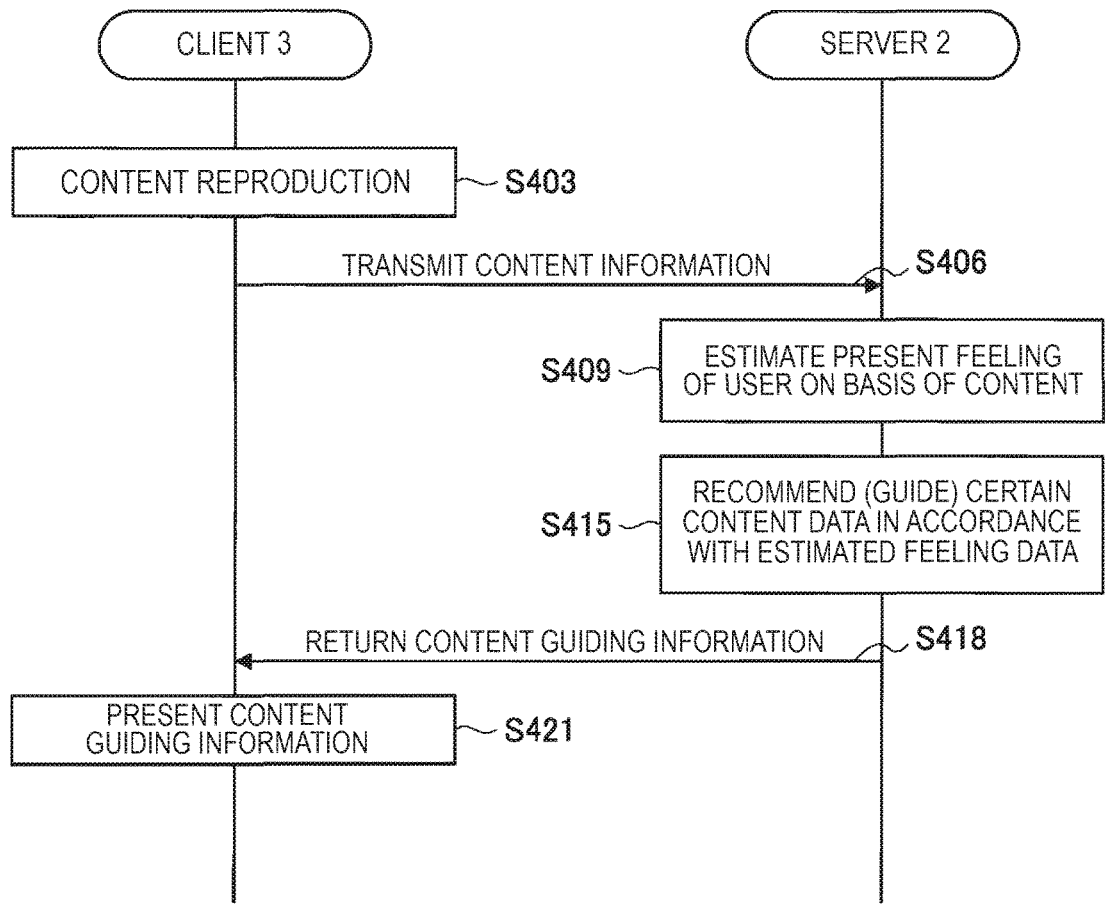
FIG. 11 is a sequence diagram illustrating an operation process of content navigation.

FIG. 11 is a sequence diagram illustrating an operation process of the content navigation. As illustrated in FIG. 11, the client 1 first reproduces the content, in step S403. The reproduction of the content data may be performed in response to user operation. Here, the client 1 is configured with the smartphone illustrated in FIG. 1, and performs the reproduction of the content data by using the display unit 12 and the audio output unit.

Thereafter, the client 1 transmits the information (the content data, the metadata, etc.) of the content in reproduction, to the server 2, in step S406. Note that the transmission of the content information may be performed automatically, and may be performed when a navigation execution instruction by the user is recognized.

Thereafter, the feeling estimation unit 20c of the server 2 estimates the present feeling of the user, on the basis of the received content information, in step S409. Specifically, the feeling estimation unit 20c performs matching by using the data stored in the content-feeling DB 23, and extracts the feeling that is linked to the content that is the same as, or similar in feature value and metadata to, the content that the user views at the present moment. The feeling estimation unit 20c outputs the estimated feeling data to the guiding information generation unit 20b.

Thereafter, in step S415, the guiding information generation unit 20b decides a certain content data to recommend (guide), in accordance with the feeling data estimated by the feeling estimation unit 20c. For example, when the music that the user listens to at the present moment evokes sad feeling, the guiding information generation unit 20b recommends (guides) content data (photograph, video, music, etc.) that evokes joyful happy feeling to the contrary. Moreover, when the present position information of the user is also transmitted from the client 1, the server 2 side can understand the present position of the user, and therefore the guiding information generation unit 20b can also recommend a movie that is playing at a movie theater around the present position of the user. The guiding information generation unit 20b generates content guiding information that includes the information of the decided recommendation (guidance) content, and outputs the generated content guiding information to the supply unit 20d.

Thereafter, in step S418, the supply unit 20d executes control to transmit the content guiding information generated by the guiding information generation unit 20b from the communication unit 21 to the client 1.

Then, in step 4221, the client 1 presents the received content guiding information, and performs guidance (recommendation) of the content. Specifically, for example, when the client 1 is the eyeglass HMD, the client 1 displays the content information that is recommended for the user on the basis of the guiding information, on a part of the display unit 12 for which transmittance is controlled. For example, presentation of the content itself, and presentation of an advertisement screen image and a purchase screen image of the content can be performed. Alternatively, for example, when the client 1 is the eyeglass HMD, a guiding information image may be superimposed and displayed on the scenery of the real space that can be visually confirmed via the display unit 12 for which transmittance is controlled. The following will be described with reference to FIG. 12.

Figure 12:
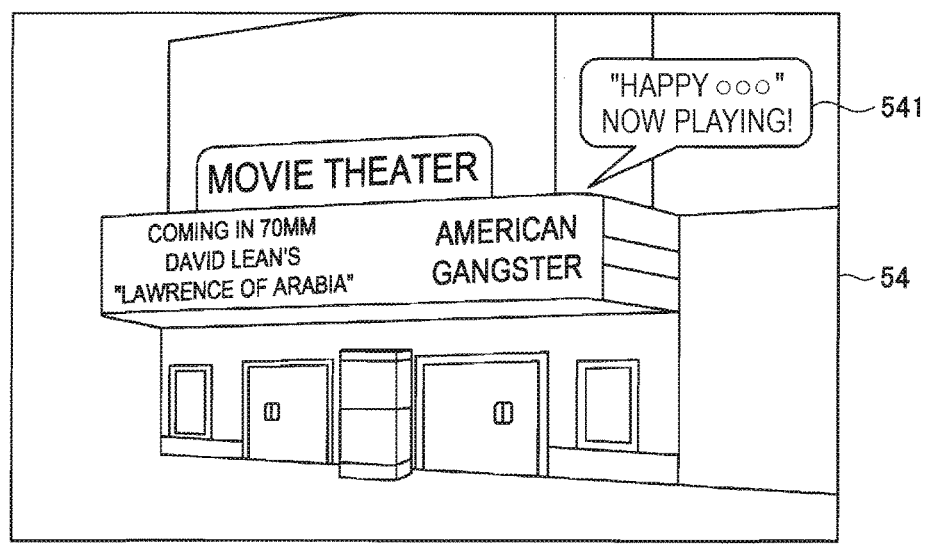
FIG. 12 is a diagram illustrating an exemplary display of content recommendation.

FIG. 12 is a diagram illustrating an exemplary display of content recommendation. In the example illustrated in FIG. 12, when the user passes the front of the movie theater, a guiding information image 541 that guides a movie according to the feeling of the user at the time, among the movies in the screening at the movie theater, is superimposed and displayed near the movie theater included in the scenery of the real space 54 that can be visually confirmed via the display unit 12 for which transmittance is controlled. Specifically, for example, the client 1 may acquire the movie information that is playing at the nearby movie theater, and performs matching with the guiding information transmitted from the server 2, and when a matched movie is playing, displays the guiding information image 541 illustrated in FIG. 12. Also, the client 1 may transmit the present position information to the server 2, and may acquire the movie information that is playing at the movie theater by recognizing the movie theater that exists around the user in the server 2 side, and the guiding information may be transmitted to the client 1 when the movie of the recommendation target is playing.

Also, the recommendation of the content may be presentation of an advertisement screen image and a purchase screen image of target content, in addition to the presentation of the content itself.

3-3. Environment Information Navigation

Next, navigation (proposal) of environment information will be described with reference to FIGS. 13 to 15.

3-3-1. Data Collection

Figure 13:
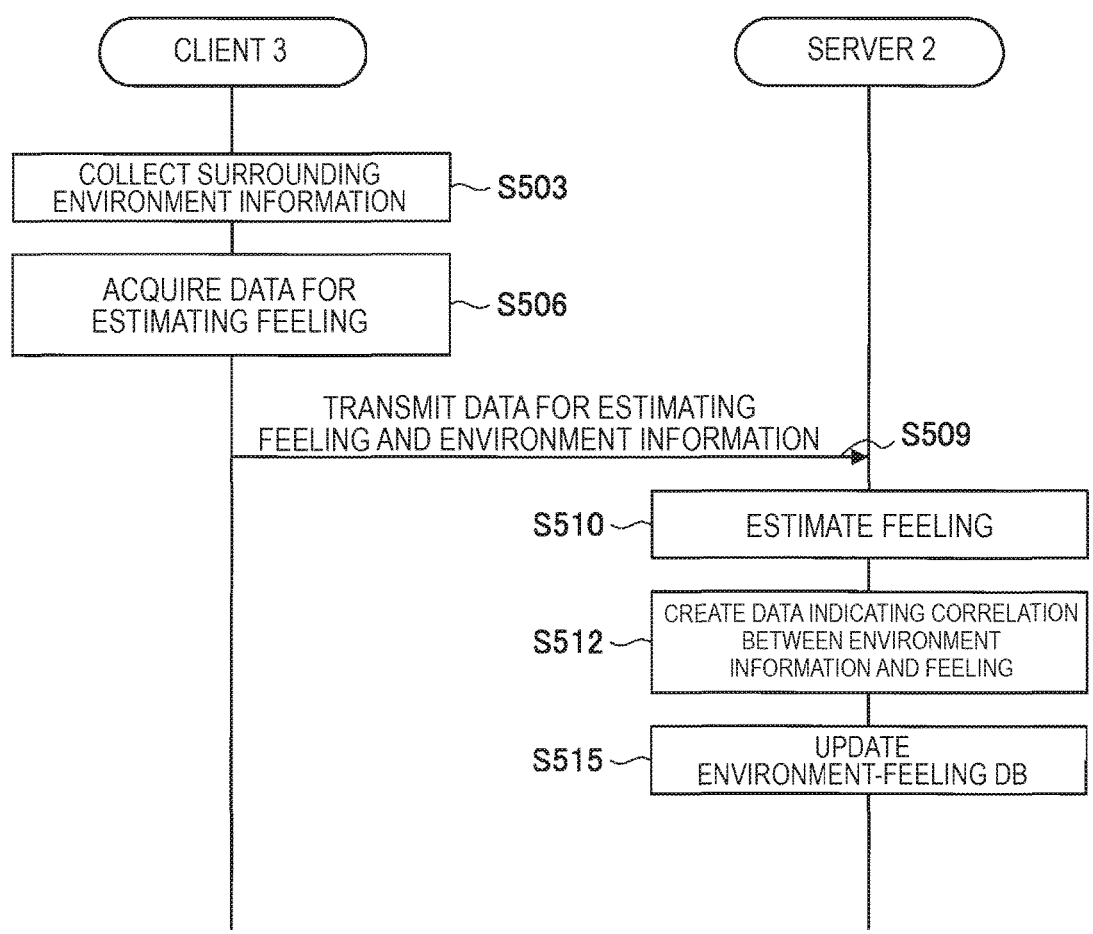
FIG. 13 is a sequence diagram illustrating an operation process at the time of data creation of an environment-feeling DB.

FIG. 13 is a sequence diagram illustrating an operation process at the time of data creation of the environment-feeling DB 22. As illustrated in FIG. 13, the data collection clients 3 first collects surrounding environment information, in step S503. Collecting of the environment information may be performed periodically or continually, and may be triggered and performed by environment change such as position movement, and may be performed in response to user operation. The clients 3 collects information such as time, position, air pressure, air temperature, degree of humidity, position, an object that exists around, a state of the object for example, as the information (field information) of the environment that surrounds the user.

Thereafter, the clients 3 acquires the data for estimating the feeling of the user, in step S506. Specifically, in the case of the client 3b configured with the smartphone illustrated in FIG. 1 for example, the acquisition is performed by a feeling sensor unit that contacts with the hand of the user that holds the client 3b and detects the perspiration, the temperature, the pulse, or the like of the user, and an in-camera provided toward inside to capture an image of the face of the user that browses photographs and videos.

Thereafter, the clients 3 transmits the data for estimating the feeling, and the environment information, to the server 2, in step S509.

Subsequently, the control unit 20 of the server 2 estimates the feeling of the user, on the basis of the received data (the face image and the biometric information) for estimating the feeling, in step S510. Note that the feeling estimation of the user may be performed at the clients 3 side, and in this case the feeling that is estimated already is transmitted to the server 2, and thus S510 is omitted.

Thereafter, in step S512, the control unit 20 creates data indicating the correlation between the environment information and the feeling. That is, the control unit 20 learns what feeling the user has under what environment information.

Thereafter, in step S515, the control unit 20 stores the generated data (learning result) in the environment-feeling DB 22, and updates the database. Steps S503 to S515 described above are performed repeatedly, and the control unit 20 continues updating the environment-feeling DB 22, on the basis of the environment information and the feeling data transmitted from each client 3 continually. In the present embodiment, the data indicating what environment information evokes what feeling can be generated more accurately, by statistically analyzing a large amount of environment information and feeling data that are collected continually from the myriad of clients 3 that are connected via the network 5.

3-3-2. Navigation

Next, navigation that uses the generated data of the environment-feeling DB 22 will be described with reference to FIGS. 14 to 15. In the environment information navigation according to the present embodiment, an improvement notification of the environment information, or an improvement idea of the environment information for leading the user to the predetermined feeling is supplied (guided) to the user.

Figure 14:
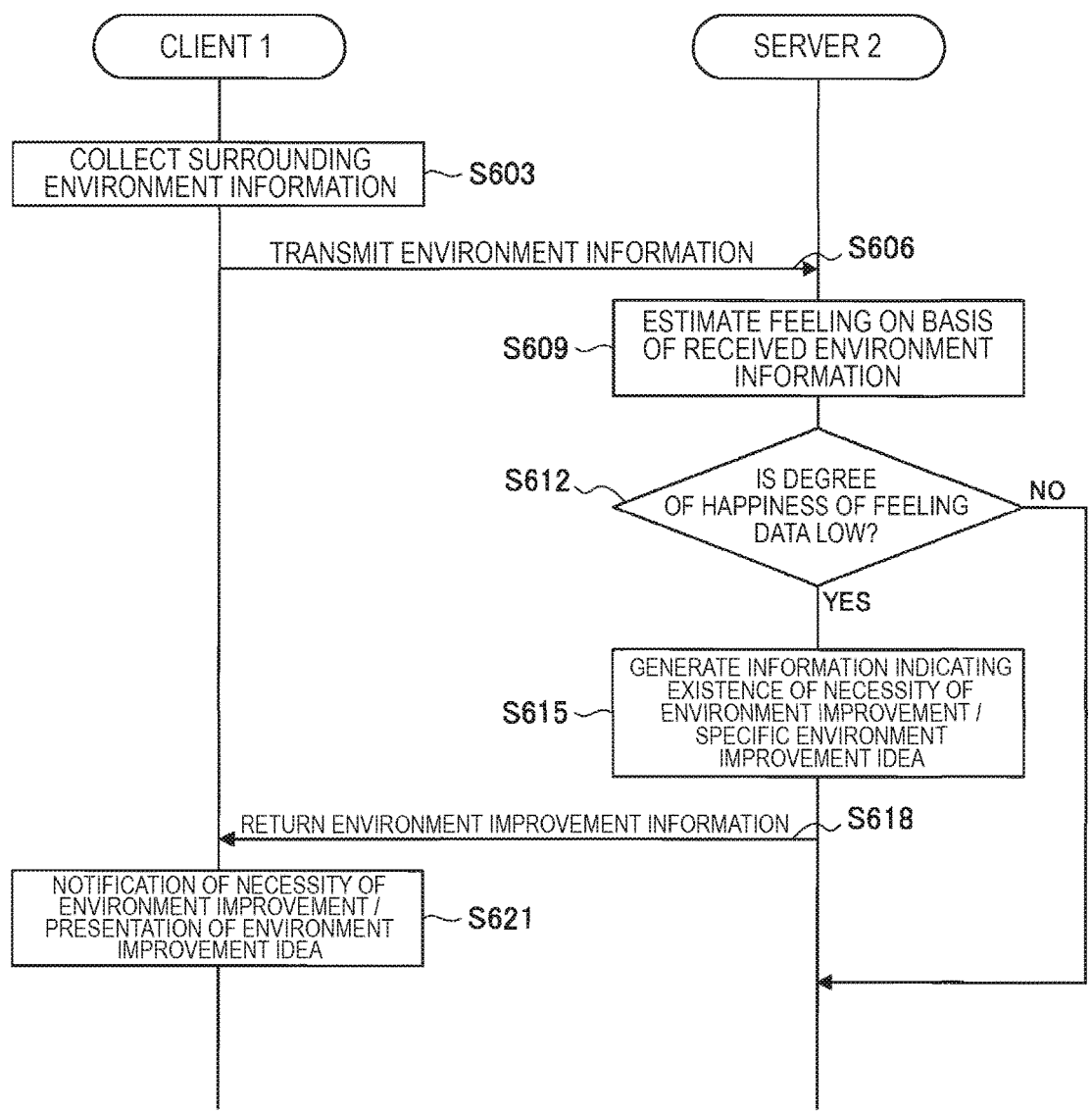
FIG. 14 is a sequence diagram illustrating an operation process of environment information navigation.

FIG. 14 is a sequence diagram illustrating an operation process of the environment information navigation. As illustrated in FIG. 14, the client 1 first collects the surrounding environment information, in step S603. The collecting of the environment information may be performed periodically or continually, and may be triggered and performed by environment change such as position movement, and may be performed in response to the user operation (the navigation execution instruction by the user).

Thereafter, the client 1 transmits the environment information to the server 2, in step S606.

Thereafter, the feeling estimation unit 20c of the server 2 estimates the present feeling of the user, on the basis of the received environment information, in step S609. Specifically, the feeling estimation unit 20c performs matching by using the data stored in the environment-feeling DB 22, and extracts the feeling linked to the environment information that is the same as or similar to the present environment surrounding the user. The feeling estimation unit 20c outputs the estimated feeling data to the guiding information generation unit 20b.

Thereafter, in step S612, the guiding information generation unit 20b deter mines whether or not the degree of happiness of the feeling data estimated by the feeling estimation unit 20c is lower than a threshold value. Here, in the present embodiment, the degree of happiness of the feeling data is determined, to perform the navigation for having the happy feeling, as an example. If the degree of happiness exceeds the threshold value (S612/No), the user already has happy feeling, and thus it is determined that the navigation is unnecessary.

On the other hand, if the degree of happiness is lower than the threshold value (S612/Yes), the guiding information generation unit 20b generates existence of the necessity of the environment improvement, or environment improvement information indicating a specific environment improvement idea, and outputs to the supply unit 20d, in step S615.

A specific environment improvement idea is generated by detecting the difference between the present environment information around the user and the environment information to which the target degree of happiness is linked (correlated) for example. For example, when gloomy feeling is estimated by the environment information when the user enters into a room of a hotel of a visit destination (the degree of happiness is equal to or smaller than a threshold value), the guiding information generation unit 20b detects the difference between the environment information and the environment information that has a correlation with the happy feeling. In this case, for example, the brightness of the room, the air temperature, the degree of humidity, open or close of windows, open or close of curtains, the presence or absence of music, and the like can be detected as the difference. The guiding information generation unit 20b generates the environment improvement information indicating making the room brighter, set values of the air temperature and the degree of humidity, opening the windows, opening the curtains, playing the music, or the like, as the environment improvement idea, for example, on the basis of this difference.

Thereafter, in step S618, the supply unit 20d executes control to transmit the environment improvement information generated by the guiding information generation unit 20b from the communication unit 21 to the client 1.

Then, in step 621, the client 1 performs notification (warning) of necessity of the environment improvement, or/and the presentation of the environment improvement idea, on the basis of the received environment improvement information, Thereby, the environment for having the happy feeling can be guided to the user. When the client 1 is configured with the eyeglass HMD for example, the notification of the environment improvement and the presentation of the environment improvement idea may be displayed on a part of the display unit 12 for which transmittance is controlled, and may be superimposed and displayed on the scenery of the real space that can be visually confirmed via the display unit 12. The following will be described with reference to FIG. 15.

Figure 15:
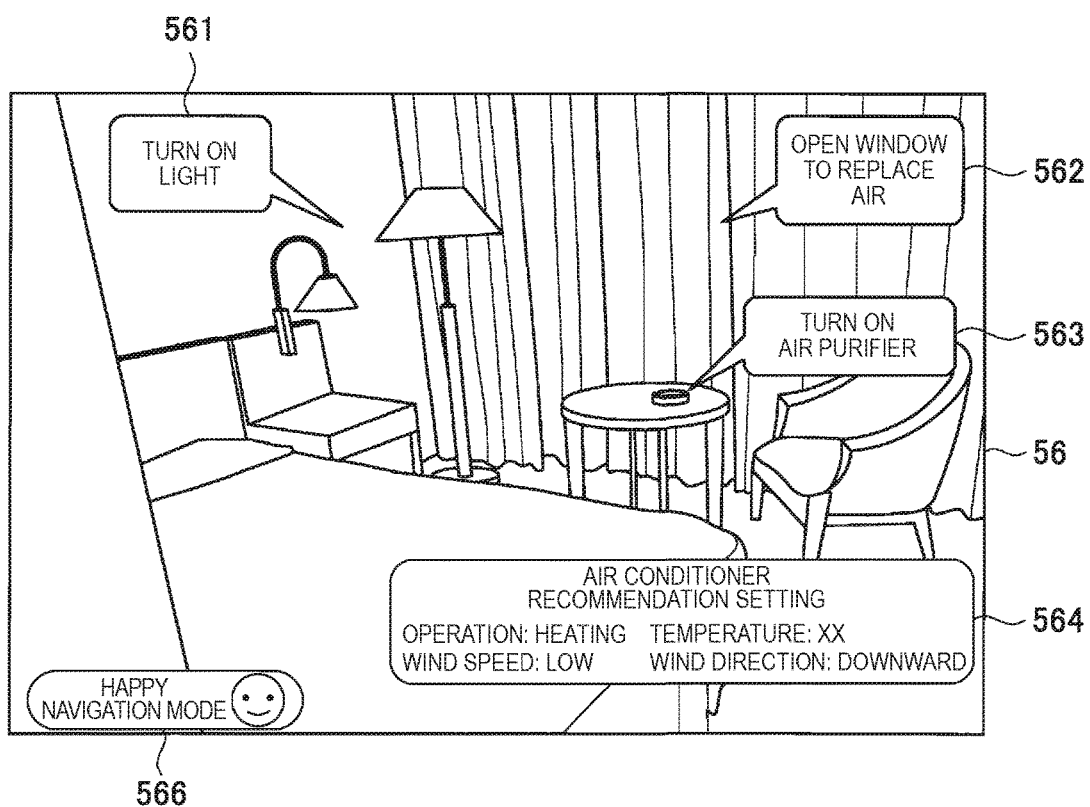
FIG. 15 is a diagram illustrating an exemplary display of environment improvement information.

FIG. 15 is a diagram illustrating an exemplary display of the environment improvement information. In the example illustrated in FIG. 15, when the user enters into the room of the hotel, the environment improvement information is superimposed and displayed in the scenery 56 of the real space that can be visually confirmed via the display unit 12 for which transmittance is controlled. For example, environment improvement information 561 such as "turn on light" is displayed near the desk lamp, and environment improvement information 562 such as "open window to replace air" is displayed near the window/curtain. Also, the environment of a smoking room is estimated from the fact that an ashtray is put on the table, and environment improvement information 563 such as "turn on air purifier" is displayed near the ashtray. Moreover, environment improvement information 564 indicating the recommendation setting information of the air conditioner is also displayed.

Further, as illustrated in FIG. 15, an icon image 566 indicating that the navigation according to the present embodiment is starting its operation may be displayed.

5. Conclusion

As described above, in the communication system according to the embodiment of the present disclosure, the action for having the predetermined feeling can be guided to the user in accordance with the feeling map. That is, the communication system according to the present embodiment presents, to the user, the guiding information that guides to the site and the area to which the predetermined feeling is linked, among a plurality of routes around the user or to the destination place, with reference to the present position information and the feeling map that are received from the client 1.

Also, in the present embodiment, viewing a certain content can be guided to the user to evoke the predetermined feeling, in accordance with the database indicating the correlation between the content and the feeling. That is, the communication system according to the present embodiment estimates the present feeling of the user with reference to the content information that the user views at the present moment which is received from the client 1 and the content-feeling DB 23, and recommends the user the content that evokes happy feeling, when the degree of happiness is low for example.

Also, in the present embodiment, the improvement of the environment can be proposed to the user to evoke the predetermined feeling, in accordance with the database indicating the correlation between the environment information and the feeling. That is, the communication system according to the present embodiment estimates the present feeling of the user with reference to the present surrounding environment information of the user which is received from the client 1 and the environment-feeling DB 22, and presents to the user the environment information for evoking happy feeling, when the degree of happiness is low for example.

Also, in the present embodiment, the present feeling of the user can be estimated on the basis of the content data or the environment information, by utilizing the environment-feeling DB 22 and the content-feeling DB 23.

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

For example, computer programs for implementing the functions of the clients 1, 3 and the server 2 can also be created in the hardware such as the CPUs, the ROMs, and the RAMs contained in the above clients 1, 3 and the server 2. In addition, a computer-readable storage medium storing the computer programs is also provided.

Also, in the present embodiment, generating the feeling map by mapping the feeling data on the map has described, but the present disclosure is not limited thereto, and for example, a lifetime map can be generated by mapping average lifetime information on the map of each area which is collected in advance. Thereby, for example, the user can be guided to the area and the site where the average lifetime is long.

Also, in the present embodiment, the feeling of the user is estimated in accordance with the content data (the photograph, the video, the music, etc.) viewed by the user, in "3-2. content navigation" but the present embodiment is not limited thereto, and for example the feeling of the user (the photographer) can be estimated in accordance with a subject image and sound acquired when the user captures an image. Specifically, for example, when the data of the correlative relationship indicating that the photographer who captures an image of a photograph of a child or an animal has happy feeling is stored as the learning result in advance in the content-feeling DB 23, the feeling estimation unit 20c can estimate the feeling of the user (the photographer) in response to the subject. Moreover, for example, when laughter or the like is detected from the sound of the subject, the subject has happy feeling, and thus the feeling estimation unit 20c, can estimate that the user (the photographer) being together also has happy feeling in the same way.

Also, each component of the clients 1, 3 and the server 2 that are included in the communication system according to the present embodiment has been described with reference to FIGS. 2 to 4, but the present disclosure is not limited thereto, and the function of each component may be dispersed in any way. Specifically, all of respective functions of the control unit 20 of the server 2 may be provided in the client 1 side for example, and the environment-feeling DB 22, the content-feeling DB 23, and the feeling map DB 24 may be provided in respective different servers.

Also, the feeling navigation that guides to the site and the route linked to the predetermined feeling in accordance with the present position information of the user has been described in "3-1. navigation according to feeling map" described above, but the present embodiment is not limited thereto. For example, the present feeling of the user can be estimated with reference to the present position information and the feeling map, in order to perform the navigation according to the estimated feeling. Specifically, when the present position is positioned at a site where the degree of happiness is low on the feeling map, the present feeling of the user is estimated to be a low degree of happiness, and the navigation to the site of a high degree of happiness is performed.

Also, in the content navigation and the environment information navigation described above, the present feeling of the user is estimated on the basis of the viewing content and the surrounding environment information respectively, but the present embodiment is not limited thereto. For example, the present feeling of the user may be estimated with reference to the present position of the user and the feeling map, in order to perform the content navigation or the environment improvement navigation to be happier.

Also, the server 2 may generate the data (the environment-feeling DB 22) indicating the correlation of the environment information and the feeling data and the data (the content-feeling DB 23) indicating the correlation of the content data and the feeling data, by the attribute (age, age period, gender, hobby, preference, place of origin, etc.) of the user.

In addition, the effects described in the present specification are merely illustrative and demonstrative, and not limitative. In other words, the technology according to the present disclosure can exhibit other effects that are evident to those skilled in the art along with or instead of the effects based on the present specification.

Additionally, the present technology may also be configured as below.

(1)
A communication system including:
an acquisition unit configured to acquire present position information of a user;
a guiding information generation unit configured to generate guiding information in accordance with the present position information and map information in which feeling data is mapped; and
a supply unit configured to supply the guiding information to the user.

(2)
The communication system according to (1), wherein the guiding information includes information that instructs the user a direction of movement according to the feeling data mapped in the map information.

(3)
The communication system according to (1) or (2), wherein
the acquisition unit acquires data for estimating the feeling of the user.

(4)
The communication system according to any one of (1) to (3), further including
a map information generation unit that generates the map information in which the feeling data is mapped.

(5)
The communication system according to (4), wherein the map information generation unit generates the map information in accordance with data for estimating the feeling of the user/the feeling data that has been estimated which is uploaded from a client, and position information.

(6)
The communication system according to (4) or (5), wherein
the map information generation unit also maps average lifetime information of each area.

(7)
The communication system according to any one of (1) to (6), further including
a first feeling estimation unit that estimates the feeling data on the basis of content data uploaded from a client.

(8)
The communication system according to (7), wherein the first feeling estimation unit estimates the feeling data according to the content data, on the basis of a learning result generated by learning a relationship between a feature value of the content data and the feeling data.

(9)
The communication system according to (7) or (8), wherein
the guiding information generation unit generates the guiding information for recommending the user certain content data according to the feeling data estimated on the basis of content data that the user views at a present moment.

(10)
The communication system according to any one of (1) to (9), further including
a second feeling estimation unit that estimates the feeling data on the basis of environment information around the user which is uploaded from a client.

(11)
The communication system according to (10), wherein the second feeling estimation unit estimates the feeling data according to the environment information, on the basis of a learning result generated by learning a relationship between the environment information and the feeling data.

(12)
The communication system according to (10) or (11), wherein
the guiding information generation unit generates the guiding information that proposes an improvement of the environment information to the user, on the basis of the feeling data estimated on the basis of present environment information around the user.

(13)
A control method including:
acquiring present position information of a user from a client;
generating guiding information in accordance with the present position information and map information in which feeling data is mapped; and
performing control to supply the guiding information to the user.

(14)
A storage medium storing a program that causes a computer to function as:
an acquisition unit configured to acquire present position information of a user;
a guiding information generation unit configured to generate guiding information in accordance with the present position information and map information in which feeling data is mapped; and
a supply unit configured to supply the guiding information to the user.

REFERENCE SIGNS LIST 1 client (for guiding information presentation)
10 control unit
11 communication unit
12 display unit
13 operation unit
14 storage unit
2 server
20 control unit
20a map information generation unit
20b guiding information generation unit
20c feeling estimation unit
20d supply unit
21 communication unit
22 environment-feeling DB
23 content-feeling DB
24 feeling map DB
3, 3a to 3c client (for data collection)
30 control unit
31 communication unit
32 display unit
33 operation unit
34 image DB
35 imaging unit
36 in-camera
37 feeling sensor unit 38 position information acquisition unit
5 network

The invention claimed is:

1. A communication system comprising:
an acquirer to acquire present position information of a user;
a guiding information generator to generate guiding information in accordance with the present position information and map information in which feeling data is mapped;
a supplier to supply the guiding information to the user; and
a first feeling estimator to estimate the feeling data on the basis of current surrounding environment information around the user,
wherein the guiding information generator generates the guiding information that proposes an improvement of the surrounding environment to the user, on the basis of the feeling data estimated on the basis of the current surrounding environment information.

2. The communication system according to claim 1, wherein
the guiding information includes information that instructs the user a direction of movement according to the feeling data mapped in the map information.

3. The communication system according to claim 1, wherein
the acquirer acquires data for estimating a feeling of the user.

4. The communication system according to claim 1, further comprising
a map information generator that generates the map information in which the feeling data is mapped.

5. The communication system according to claim 4, wherein
the map information generator generates the map information in accordance with the feeling data that has been estimated which is uploaded from the client and position information.

6. The communication system according to claim 4, wherein
the map information generator also maps average lifetime information for individuals present in different areas.

7. The communication system according to claim 1, further comprising
a second feeling estimator that estimates the feeling data on the basis of content data uploaded from the client.

8. The communication system according to claim 7, wherein
the second feeling estimator estimates the feeling data according to the content data, on the basis of a learning result generated by learning a relationship between a feature value of the content data and the feeling data.

9. The communication system according to claim 7, wherein
the guiding information generator generates the guiding information for recommending the user certain content data according to the feeling data estimated on the basis of content data that the user views at a present moment.

10. The communication system according to claim 1, wherein
the first feeling estimator estimates the feeling data according to the surrounding environment information, on the basis of a learning result generated by learning a relationship between the surrounding environment information and the feeling data.

11. A control method comprising:
acquiring present position information of a user from a client;
generating guiding information in accordance with the present position information and map information in which feeling data is mapped;
performing control to supply the guiding information to the user; and
estimating the feeling data on the basis of current surrounding environment information around the user which is uploaded from a client,
wherein the guiding information that is generated proposes an improvement of the surrounding environment to the user, on the basis of the feeling data estimated on the basis of the current surrounding environment information.

12. A non-transitory computer readable storage medium storing a program that causes a computer to function as:
an acquirer to acquire present position information of a user;
a guiding information generator to generate guiding information in accordance with the present position information and map information in which feeling data is mapped;
a supplier to supply the guiding information to the user; and
a feeling estimator to estimate the feeling data on the basis of current surrounding environment information around the user which is uploaded from a client,
wherein the guiding information generator generates the guiding information that proposes an improvement of the surrounding environment to the user, on the basis of the feeling data estimated on the basis of the current surrounding environment information.

* * * * *